(12) United States Patent
Nurse et al.

(10) Patent No.: US 10,071,274 B2
(45) Date of Patent: Sep. 11, 2018

(54) JUMP ROPE DEVICE

(71) Applicants: Philip Nurse, Brooklyn, NY (US); Alfredo Antonio Perez de Alejo, III, Springfield, NJ (US); Aaron Perez-Daple, Springfield, NJ (US); Brian James Cunningham, Medford, NJ (US); Robert Andres Blinn, New York, NY (US); Kamuti Kiteme, New York, NY (US)

(72) Inventors: Philip Nurse, Brooklyn, NY (US); Alfredo Antonio Perez de Alejo, III, Springfield, NJ (US); Aaron Perez-Daple, Springfield, NJ (US); Brian James Cunningham, Medford, NJ (US); Robert Andres Blinn, New York, NY (US); Kamuti Kiteme, New York, NY (US)

(73) Assignee: Gravity Rope, LLC, Springfield, NJ (US)

( * ) Notice: Subject to any disclaimer, the term of this patent is extended or adjusted under 35 U.S.C. 154(b) by 0 days.

(21) Appl. No.: 15/219,266

(22) Filed: Jul. 25, 2016

(65) Prior Publication Data

US 2017/0028241 A1    Feb. 2, 2017

Related U.S. Application Data

(60) Provisional application No. 62/196,711, filed on Jul. 24, 2015, provisional application No. 62/301,628, filed on Mar. 1, 2016.

(51) Int. Cl.
*A63B 5/20* (2006.01)
*A63B 5/22* (2006.01)
(Continued)

(52) U.S. Cl.
CPC .......... *A63B 5/20* (2013.01); *A63B 21/00061* (2013.01); *A63B 21/0601* (2013.01);
(Continued)

(58) Field of Classification Search
CPC ..... A63B 5/20; A63B 5/205; A63B 21/00043; A63B 21/0442; A63B 21/0407; A63B 21/0414; A63B 21/421
See application file for complete search history.

(56) References Cited

U.S. PATENT DOCUMENTS 1,651,057 A * 11/1927 Goldstein ................ A63B 5/20
                                                      482/82
3,064,972 A    11/1962 Feinn
(Continued)

OTHER PUBLICATIONS

PCT/US 17/20096, International Search Report, ISA/210, dated Jul. 6, 2017.
(Continued)

*Primary Examiner* — Nyca T Nguyen
(74) *Attorney, Agent, or Firm* — Aaron Perez-Daple

(57) ABSTRACT

An adjustable-length jump rope device that provides the benefits of a speed rope and weighted rope in one device by, among other things, allowing the rotational resistance of the jump rope to be varied without affecting the circumference of the rope and by distributing the weight of the rope evenly, thus, enabling smooth and natural jumping.

10 Claims, 18 Drawing Sheets

(51) Int. Cl.
*A63B 23/16* (2006.01)
*A63B 22/14* (2006.01)
*G06F 19/00* (2018.01)
*A63B 21/06* (2006.01)
*H02N 2/18* (2006.01)
*A63B 21/00* (2006.01)
*A63B 71/06* (2006.01)
*A63B 71/00* (2006.01)

(52) U.S. Cl.
CPC ........... *G06F 19/3481* (2013.01); *H02N 2/18* (2013.01); *A63B 71/0622* (2013.01); *A63B 71/0686* (2013.01); *A63B 2071/009* (2013.01); *A63B 2071/0625* (2013.01); *A63B 2071/0655* (2013.01); *A63B 2071/0694* (2013.01); *A63B 2207/02* (2013.01); *A63B 2220/17* (2013.01); *A63B 2225/09* (2013.01); *A63B 2225/50* (2013.01); *A63B 2230/06* (2013.01); *A63B 2230/30* (2013.01); *A63B 2230/75* (2013.01)

(56) References Cited

U.S. PATENT DOCUMENTS

| | | | | |
|---|---|---|---|---|
| 4,177,985 A * | 12/1979 | Hlasnicek | .............. | A63B 5/20 482/110 |
| 4,375,886 A * | 3/1983 | Muys | .............. | A63B 5/20 482/82 |
| 4,505,474 A | 3/1985 | Mattox | | |
| 4,776,585 A * | 10/1988 | Maleyko | .............. | A63B 5/20 200/11 G |
| 4,872,666 A | 10/1989 | Smith | | |
| 4,890,829 A | 1/1990 | Burton | | |
| 4,919,417 A | 4/1990 | Poulas | | |
| 5,102,381 A * | 4/1992 | Danielak | .............. | A63B 5/20 446/15 |
| 5,224,910 A | 7/1993 | Deutsch | | |
| 5,662,561 A * | 9/1997 | McNamara | .............. | A63B 5/20 482/82 |
| 5,842,956 A * | 12/1998 | Strachan | .............. | A63B 5/20 482/81 |
| 6,544,148 B1 | 4/2003 | Loew | | |
| 6,595,900 B1 * | 7/2003 | Cook | .............. | A63B 5/20 482/126 |
| 7,628,735 B1 * | 12/2009 | Hsu | .............. | A63B 5/20 482/108 |
| 8,043,196 B1 * | 10/2011 | Chen | .............. | A63B 5/20 482/121 |
| 8,911,333 B2 | 12/2014 | Hunt | | |
| 9,056,216 B1 * | 6/2015 | Bouza | .............. | A63B 5/20 |
| 9,550,086 B1 * | 1/2017 | Poirier | .............. | A63B 5/20 |
| 2003/0148859 A1 * | 8/2003 | Chun | .............. | A63B 5/20 482/82 |
| 2013/0245144 A1 * | 9/2013 | Chow | .............. | A63H 33/00 521/110 |

OTHER PUBLICATIONS

PCT/US 17/20096, Written Opinion and Search History, ISA/237, dated Jul. 6, 2017.

* cited by examiner

JUMP ROPE DEVICE

REFERENCE TO RELATED APPLICATIONS

This application claims the benefit of U.S. provisional application Ser. Nos. 62/196,711, filed Jul. 23, 2015 and entitled "JUMP ROPE DEVICE"; and 62/301,628, filed Mar. 1, 2016 and entitled "JUMP ROPE DEVICE," the entire contents of which are hereby incorporated by reference.

FIELD OF INVENTION

The present disclosure relates to jump ropes.

BACKGROUND

Jumping rope can provide an effective aerobic and anaerobic workout that also improves coordination, agility, and footwork. To fully realize the benefits of jumping rope, a jump rope user usually has to actively switch between different types of ropes.

For example, lightweight ropes, sometimes referred to as "speed ropes," can be rotated quickly, allowing users to focus on cardiovascular fitness, while simultaneously developing coordination and speed. But such lightweight ropes fail to provide any significant muscle strengthening and endurance benefits to the upper-body because the force required to rotate the rope is relatively small.

Heavier ropes, sometimes referred to as "heavy ropes" or "weighted ropes," require greater force to rotate, which improves muscle strength, endurance, and tone in the upper body, in particular in the forearms, biceps, and shoulders. But such heavy ropes cannot be rotated very quickly and, thus, fail to provide the cardiovascular benefits of speed ropes. Moreover, the slower rotation of heavy ropes makes it difficult, if not impossible, to perform movements that target coordination, agility, and footwork, such as double-jumps (or double-unders).

In addition, as a user becomes acclimated to the weight of a weighted rope, he or she may need to buy additional ropes, each of increasingly heavier weight, in order to continue to improve muscle strength and endurance. Further, as a user becomes more skilled at jumping rope, a shorter rope is often needed, which may require purchasing multiple rope(s) of varying length. Thus, a user may need to ultimately purchase multiple weighted ropes and multiple speed ropes, in order to fully realize the benefits of jumping rope. Similarly, gyms and other fitness facilities may need to purchase and maintain multiple jump ropes of varying lengths (and weights) in order to accommodate differences in their clientele's heights, strength, and skill levels.

Currently, no jump rope device exists which can provide the benefits of a speed rope and weighted rope in one device, while allowing a user to progressively increase the weight and, optionally, decrease (or increase) the length of the jump rope.

Some weighted jump rope devices allow users to increase the weight of a jump rope by adding sand or water. While this allows a user to increase the weight of the rope, the sand or water has a tendency to settle towards the center of the rope portion, making the distribution of weight uneven throughout the rope. This uneven distribution of weight makes jumping rope awkward, and impedes a user's ability to achieve and maintain a smooth and natural rotation of the jump rope. In addition, it is difficult for a user to gauge the exact weight he or she is adding to the rope, because of the difficulty in determining the exact amount of material (e.g., water or sand) being added to the rope and the material's weight. Therefore, it is difficult to uniformly increase, or scale-up, the weight of the jump rope. It is also cumbersome to travel with such devices or to use such devices in various training environments, as they require either traveling with sand or water, or training in areas where you can get ready access to such materials. Moreover, such devices do not lend themselves to speed rope style training, and therefore, do not provide the same cardiovascular and speed training benefits as a speed rope.

Some weighted jump rope devices allow a user to adjust the weight of each handle. But, while providing some increase in resistance, increasing the weight of the handles fails to provide the same resistive force as increasing the weight of the rope portion of the jump rope, and therefore, is not as effective an upper body workout as increasing the weight of the rope portion. In addition, because the weight is in the handles as opposed to the rope portion, such devices impede a user's ability to smoothly and naturally rotate the jump rope.

Other weighted jump rope devices allow a user to adjust the weight of the rope portion of the jump rope by adding counter-weights to set areas of the rope portion. This again results in an uneven distribution of weight throughout the length of the jump rope, making it awkward for a user to jump rope, and difficult to achieve a smooth and natural rotation of the jump rope.

Still other weighted jump rope devices require a user to change the entire rope portion of the jump rope in order to change the weight of the jump rope. The rope portion of such devices typically comprise a metal cable that can attach to each of two handles. Such metal cables tend to be expensive as, among other things, each cable includes its own separate mechanism (e.g., a metal clip) for attaching the cable to each handle. In addition, the cables typically have different diameters and properties that affect the performance and feel of the device, requiring users to adjust their jumping style whenever the cable is changed. Moreover, the rotational mechanisms in such ropes (e.g., ball bearings) typically allow for easy rotation by momentum, reducing the resistance provided by the rope and thus reducing the benefits of increasing the weight. Such devices also suffer from the problem that the cables themselves are quite hard and can injure and/or cause pain to a user if they strike the feet or head while jumping rope.

Another problem with known jump ropes is that there is no easy mechanism for users to track their workouts and determine when their goals have been reached. Users typically have goals in mind for their workouts, such as jumping rope for a certain amount of time. However, when a user is working out on his or her own, it is difficult to accurately measure the time intervals when jumping rope. Typically, a user will need a separate timer, which he or she has to monitor and control. This can be difficult, because jumping rope is an activity that requires the use of both hands. Thus, when using a timer, a user needs to first start the timer and then must pick up the rope and begin jumping. A user must also monitor the timer to determine when the time has elapsed. Of course, picking up the rope and starting to jump itself takes time, which causes the timer to be inaccurate as a measure of the exercise interval. If the user fails to notice when the timer has expired, this will also cause inaccurate results. Moreover, using a separate timer (or other stand-alone measurement device) is inconvenient for the user, because it complicates the workout and requires an extra device.

Accordingly, there is a need for a jump rope device capable of providing the cardiovascular benefits—along with the coordination, agility, speed, and footwork training capabilities—of a speed rope, with the strength and muscle endurance benefits of a weighted rope. In addition, there is a need for a jump rope device that allows a user to scale up his or her workout by progressively increasing the rotational resistance provided by the rope while jumping. There is also a need for a jump rope that allows a user to easily track his or her workouts and determine when his or her goals have been reached, without requiring a separate device during the workout. Moreover, there is a need for a jump rope that allows a user (or multiple users) to easily adjust the length of the jump rope to fit the user's height, strength, and/or skill level.

The present disclosure is directed to jump rope devices that address these and other problems in the art.

SUMMARY

The present disclosure includes embodiments of jump rope devices that provide the benefits of a speed rope and weighted rope in one device. Jump rope devices in accordance with some embodiments of the present disclosure enable users to develop speed and improve their cardiovascular health, while also developing their muscular strength and endurance. Such jump rope devices may provide these benefits by, among other things, allowing the rotational resistance of the jump rope to be varied without affecting the circumference of the rope and by distributing the weight of the rope evenly, thus, enabling smooth and natural jumping. Moreover, jump rope devices in accordance with such embodiments of the present disclosure allow for the quick rotation of the rope—similar to a speed rope—while providing sufficient resistance to work the upper body—similar to a heavy rope. Alternatively, jump rope devices in accordance with some embodiments of the present disclosure may be designed to operate primarily as a speed rope or heavy rope, rather than serving both functions.

The present disclosure includes embodiments designed to optimize the balance between the speed of rotation of the rope portion of the jump rope and the weight of the jump rope to provide the benefits of both a speed rope and a weighted rope in a single device. For example, some embodiments may require more rotational force to be applied to the handles during jumping, for a given weight of the rope, than in conventional ropes. As a result, it is possible to use a lower weight for the rope to achieve the same strengthening benefits as a heavier rope in conventional designs. Because the rope portion weighs less, it is also possible to rotate the rope at higher speeds sufficient to perform techniques such as double-jumps. Rotating the rope at higher speeds also enhances the upper body workout, because it requires more rotations (or repetitions) over the same period of time. The present disclosure describes embodiments in which the design, weight, and materials of the jump rope have been selected to provide the optimal balance between speed and strengthening benefits.

Embodiments of jump rope devices in accordance with the present disclosure may comprise a rope portion connected, either directly or indirectly, to two handles. The first end of the rope portion may be attached to a first handle, while the second end of the rope portion may be attached to a second handle. The rope portion may be hollow, and may include at least one opening through which a weighted core may be removably inserted and disposed within the rope portion. In some embodiments, the rotational resistance of the jump rope may be varied by changing the weight of the weighted core inserted into the rope portion—or by removing the weighted core altogether.

In some embodiments, one or more weighted cores may be inserted into the rope portion of the jump rope, and weighted cores of varying weights and materials may be used with the jump rope device. Different-weight weighted cores may provide varying resistance. For example, by varying the weight of the weighted cores, a user may increase the rope's weight, and therefore the jump rope's rotational resistance, thereby making it more difficult to complete a rotation of the rope. In this way, by progressively increasing the weight of the weighted core, a user may progressively increase his or her upper body strength and endurance.

Jump rope devices in accordance with some embodiments of the present disclosure may also include electronics disposed in one or more of the handles. The electronics may determine when a user's workout goals have been met and may provide a sensory output (e.g., vibration, noise, or light) to notify the user. In some embodiments, electronics in the jump rope may automatically detect when a user has started jumping rope, and may start a timer (or begin counting jumps or calories burned, for example); when the timer expires (or other target has been met), electronics in the jump rope may activate a vibration device in the handle (or other sensory output device), thereby notifying the user.

Electronics provided in various embodiments of the jump rope may serve other functions, as well, such as allowing users to playback stored audio files (e.g., MP3) through a headset attached to a jack in the handle. Electronics in the jump rope may also provide a visual display (e.g., through an LCD screen disposed in the handle) and may allow a user to provide input (e.g., through a control panel disposed in the handle). Electronics in the jump rope may also communicate with an application or program running on a computer or other electronic device by a direct (e.g., USB) or wireless (e.g., Wi-Fi, Bluetooth) connection, thereby allowing information to be shared between devices. In such ways, a user may control and/or view information about their workouts, either on the jump rope display or on another device (e.g., smartphone, computer, watch).

Jump rope devices in accordance with some embodiments of the present disclosure may also include a handle (or handles) that enables the length of the rope portion outside the handle to be adjusted to fit a user's height or skill level. In one such embodiment, the length of the jump rope may be increased, or conversely decreased, by securing the end of the rope portion of the jump rope within a chamber inside the handle corresponding to a desired length of the jump rope portion to be disposed outside of handle.

Various objects, features, embodiments, and advantages of the present disclosure will become more apparent from the following detailed description, along with the accompanying drawings. The present Summary, while providing an introduction to various embodiments of the present disclosure, is not intended to limit the scope of the subject matter to be claimed. Further advantages of the present disclosure will be apparent to a person of skill in the art in view of the foregoing disclosure.

DETAILED DESCRIPTION

Figure 1:
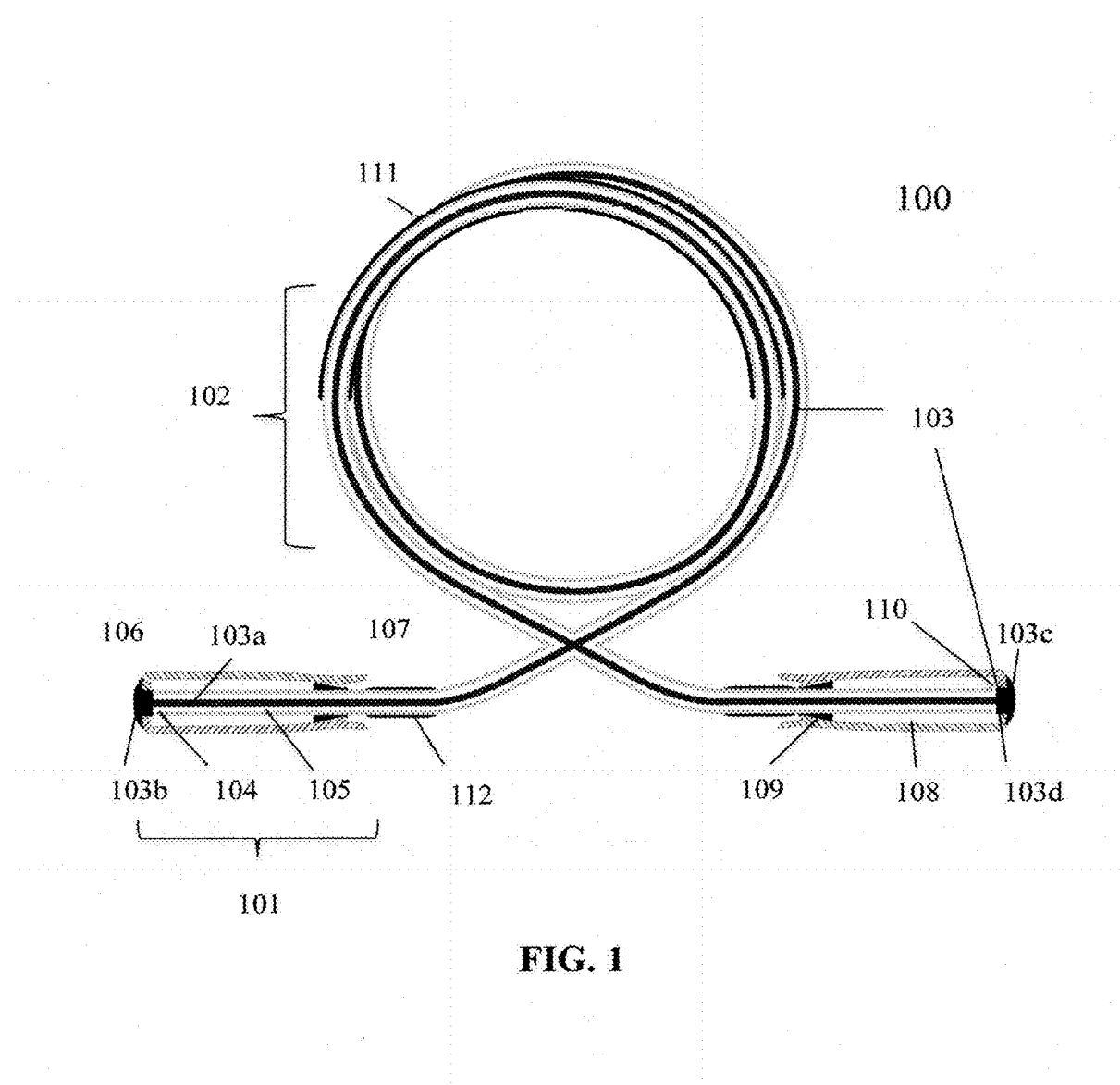
FIG. 1 is a front view of an example of a jump rope device in accordance with aspects of the present disclosure.

FIG. 1 shows a front view of an example of a jump rope 100 in accordance with aspects of the present disclosure. The jump rope 100 comprises a rope portion 102 connected to two handles 101. Rope portion 102 may comprise a hollow tube that extends between the handles 101. Rope portion 102 may also include an opening 104 through which a weighted core 103 may be inserted into rope portion 102. In other embodiments, rope portion 102 may include more than one opening 104 through which one or more weighted cores 103 may be inserted into rope portion 102.

Rope portion 102 may be made of any material that is sufficiently aerodynamic, flexible, and durable to be used as the rope portion of a jump rope. Such materials may include, without limitation, plastics, rubber, elastomers, aramids (such as Kevlar, Nomex, and Technora), and/or any hybrid of such materials, or any other similar materials as will be apparent to those skilled in the art after reading the present disclosure. In some embodiments, rope portion 102 may be made of a material (or materials) with a durometer between Shore 65 and Shore 85, which advantageously may mitigate injury, pain, and/or discomfort caused to users upon accidentally striking themselves with rope portion 102 of jump rope 100. In a preferred embodiment, rope portion 102 is comprised of a material with a durometer between Shore 68 and Shore 75, which may provide an optimal balance between elasticity and durability of the rope portion 102.

Rope portion 102 may vary in length. However, in some embodiments, rope portion 102 may be between 8' and 10' in length, depending on a user's height. For example, if a user is 5'8" or shorter in height, rope portion 102 may be 8'6" or shorter. Alternatively, if a user is between 5'8" and 6'2" in height, rope portion 102 may be between 8'6" and 10', and preferably around 9'3" in length. If a user is over 6'2" in height, rope portion 102 may be 10' or longer in length. Notwithstanding the foregoing, the length of rope portion 102 may be of any length suitable for jumping rope, including lengths that do not fall within the 8' and 10' range.

Rope portion 102 may be any width or diameter that allows jump rope 100 to function as a jump rope, as would be understood by a person of skill in the art in view of the present disclosure. In some embodiments, rope portion 102 may have a diameter of between about 0.5 and 0.75 inches.

Rope portion 102 may include hollow portion 105 that extends the length of rope portion 102, and an opening 104, through which a removable weighted core 103 may be inserted into hollow portion 105. Hollow portion 105 and opening 104 may be any size that allows removable weighted core(s) 103 to be inserted into rope portion 102, while still allowing rope portion 102 to function as the rope portion of jump rope 100. For example, in some embodiments, hollow portion 105 and opening 104 may have a diameter between 0.30 and 0.40 inches, and preferably a diameter of between 0.375 to 0.395 inches. While hollow portion 105 and opening 104 may have equal sizes or diameters, in some embodiments, the size of hollow portion 105 may differ from the size of opening 104.

Notably, while this disclosure uses the term "diameter" throughout, the present invention is not limited to circular or cylindrical shapes. As would be understood by a person of skill in the art in view of the present disclosure, embodiments of the present disclosure may incorporate openings, bores, apertures, and hollow portions of various shapes, including squares, ovals, pentagons, hexagons and so forth. Similarly, in some embodiments, rope portion 102 may have a cross-sectional shape that is not circular or cylindrical.

Rope portion 102 may be transparent, or may be sufficiently translucent so as to allow the contents of rope portion 102, including weighted core 103, to be visible. In some embodiments, the color of weighted core 103 may be varied according to its weight, thereby allowing a user to visibly determine the weight of weighted core 103 (or the weight of jump rope 100 when weighted core 103 is inserted into rope portion 102). Weighted core 103 also may include markings on its surface (such as text, numbers, or lines) indicating its weight (or the weight of jump rope 100 when weighted core 103 is inserted into rope portion 102). In this way, a user can easily determine the weight of removable weighted core 103 (and/or the weight of jump rope 100) without having to remove weighted core 103 from jump rope 100.

In other embodiments, rope portion 102 may change color, or hue, when weighted core 103 is inserted. This may be achieved by, for example, utilizing a translucent (or semi-translucent) rope portion 102 of one color (e.g., blue) in conjunction with a weighted core 103 of another color (e.g., yellow). In such an example, adding weighted core 103 to rope portion 102 may make rope portion 102 appear a different color (e.g., green). The color that rope portion 102 appears to change into may correspond to the weight of weighted core 103 (or weight of jump rope 100, when weighted core 103 is inserted). Thus, a user can know the weight of weighted core 103 (and/or the weight of jump rope 100) without having to remove weighted core 103 from jump rope 100.

In yet other embodiments, rope portion 102 may be opaque or non-transparent, and may be any color. Rope portion 102 may also include markings on its surface (such as text, numbers, or lines), including, for example, markings indicating the weight of jump rope 100, the owner of the rope, or a brand, gym, or school affiliated with the owner, manufacturer, or distributor of jump rope 100.

Moreover, when rope portion 102 is transparent or sufficiently translucent, weighted core(s) 103 having special visual characteristics may be used. For example, weighted core(s) 103 may be fluorescent, phosphorescent, or glow in the dark. In other embodiments, weighted core(s) 103 may incorporate lights, such as light emitting diodes (LEDs). By incorporating electronics into jump rope 100, such lights may be configured to light up as jump rope 100 is used, or to light up in such a way as to display images, such as the number of revolutions achieved or calories burned by the user.

Figure 12:
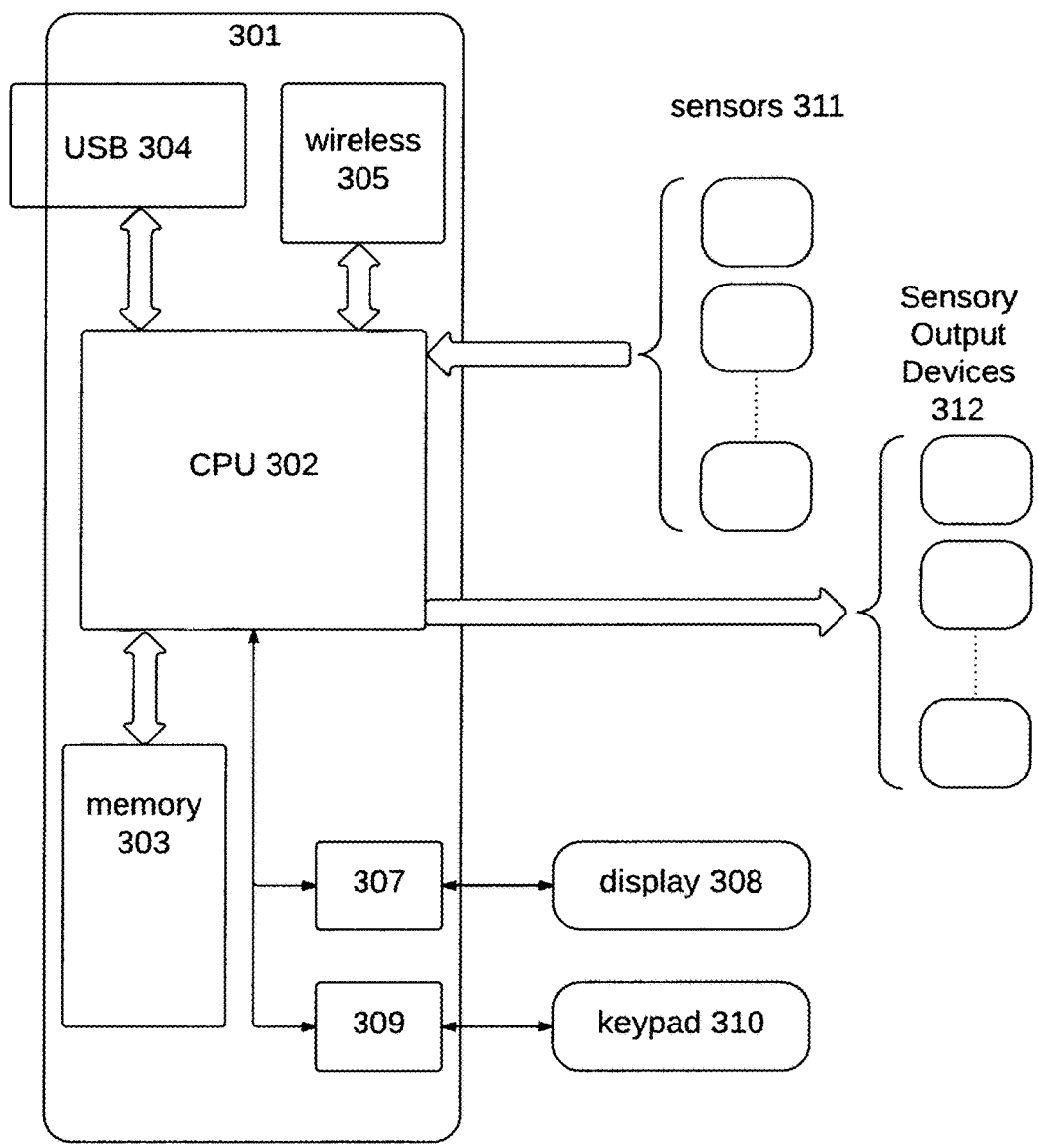
FIG. 12 shows an example of electronics, including a circuit board, sensors, and sensory output devices, used in aspects of the present disclosure.

In some embodiments, electronics 300 may be provided in at least one of handles 101. As shown in FIG. 12, electronics 300 may comprise one or more of a central processing unit (CPU) 302, memory 303 (e.g., RAM, solid state memory), USB circuit 304, wireless circuit 305 (e.g., Bluetooth, Wi-Fi chipsets), display circuit 307, display 308, keypad circuit 309, keypad 310, one or more sensor(s) 311, and one or more sensory output device(s) 312. CPU 302 may receive input signals from one or more sensors 311 and send control signals to one or more sensory output devices 312. Some or all of electronics 300 may be disposed on a circuit board 301 that is suitable for insertion into handle 101.

As used herein, the term "circuit" may include any of a chipset, integrated circuit, analog circuit, digital circuit, software logic, or any hardware or software used to control electrical components of the device. Furthermore, the circuits may be integrated with, or separate from, CPU 302. As would be understood by one of skill in the art in view of the present disclosure, additional hardware, software and/or firmware may be provided to interface with various input/output devices. For example, additional circuits may be provided for interfacing with sensors 311 and/or sensory output devices 312.

One or more batteries may also be provided in handle(s) 101 for powering the electronics and attached devices (e.g., LEDs, vibration device, audio device). The batteries may comprise standard consumer batteries (e.g., AAA, AA), watch batteries, custom designed batteries, or any other suitable batteries as would be understood by a person of skill in the art in view of this disclosure. In embodiments of the invention, power generated by rotating the handles during jumping may be used to recharge batteries in handle 101, for example, using a magnetic induction mechanism to covert mechanical energy from the rotation into electrical energy used to charge the battery. This generated power may also be used to charge devices external to the handles by, for example, utilizing a battery (or batteries) that may be removed from each handle 101 and inserted into such devices, or through other means as would be understood by a person of skill in the art in view of the present disclosure (e.g., by plugging the external device directly to the handle via a USB or similar means).

Optionally, one or more wires may be passed through opening 104 to interface with sensors 311 and/or sensory output devices 312. For example, such wires may be used to exchange data, power, AC signals, and/or other information. Wires may also pass through rope portion 102 to the other of handles 101, thereby allowing data, power, AC signals, and/or other information to pass between electronic devices and/or circuits disposed in the handles 101.

CPU 302 may run software that processes input from one or more sensors 311 and stores it in memory 303. For example, CPU 302 may run software that calculates the number of rotations (or jumps), the time elapsed, and/or that estimates total calories burned. CPU 302 may compare these calculations to one or more goals set by a user (or preprogrammed or downloaded) to determine whether a goal has been met. CPU 302 may also control LEDs and/or other sensory output devices 312 to provide feedback to the user, for example, when a goal has been achieved.

By connecting electronics 300 in the jump rope to a computer or other electronic device—e.g., via USB or wirelessly—a user may download or otherwise transfer information about his or her workout that is stored in memory 303, such as the duration of the workout, the number of jumps, the rate of jumping, an estimate of calories burned, and/or timeline information about the number of jumps or calories burned per unit of time (e.g., jumps per 15 second interval). For example, when synched with an Apple™ Watch, a user may be able to view information and/or receive alerts about their workout on the watch in near real-time. In some embodiments, information may be transferred directly from CPU 302 to an electronic device, such as a smartphone or watch, without first being stored in memory 303.

Also, by connecting electronics 300 in the jump rope to a computer or other electronic device, a user may provide input or otherwise transfer information that is used by the CPU to set goals and/or perform calculations. For example, a user may input the desired duration of his or her workout or a desired amount of calories to burn into his or her smartphone, computer, or watch; this information may then be transferred to memory 303 and used by CPU 302 to control electronics 300 in the jump rope. As another example, a user may input personal information, such as his or her weight, that allows CPU 302 to estimate the number of calories burned. As yet another example, parameters for a workout session may be downloaded from the Internet (or otherwise obtained) and transferred to electronics 300 in the jump rope 100 for a particular exercise routine—e.g., a certain number of jump cycles, each with a target duration and a target rate of jumping.

In some embodiments of the present disclosure, an application (or "app") running on a computer, smartphone, watch, or other "smart" device, may be used to control the jump rope 100, for example, by selecting the parameters for an exercise routine. For example, an application may be configured to allow a user to choose from a number of different workouts, each having different durations, intervals, and intensities. Once the selection is made, the parameters for the workout may be transferred to memory 303 (e.g., via a Wi-Fi or Bluetooth connection) and used by CPU 302 to control the jump rope. Alternatively, the application may select an exercise routine for the user based on information about the user's fitness level, vital statistics (e.g., blood pressure, heart rate), and/or goals. Rather than storing the exercise parameters in memory 303, an application (or other program) may instead control the jump rope by sending real-time commands to CPU 302 (or other circuits in electronics 300). An application may also be used to monitor and track the user's results and/or fitness level over time and provide an output to the user, for example, in the form of a chart or graph.

In some embodiments, no display, keypad, or related circuitry is provided in the jump rope; rather, a user may connect electronics 300 to a computer (or other electronic device) in order to access information stored in memory 303 or otherwise interact with electronics 300. In some embodiments, the connection may be made wirelessly (e.g., via Wi-Fi or Bluetooth), and no USB circuitry is provided.

In other embodiments, display circuit 307 and display 308 (e.g., LCD or LED screen) may be provided to show the user information, such as the time interval for a workout, the number of intervals, the time elapsed, the number of jumps, the number of calories burned, and/or other similar information. Display 308 may be disposed in handle(s) 101 in one or more locations convenient for the user, such as in a top portion, bottom portion, or side portion of the handle(s) 101. Keypad circuit 309 and keypad 310 also may be provided to allow interaction with the display 308 and/or to receive other user input. For example, a user may interact with keypad 310 to select a time interval or other target for a workout. In some embodiments, keypad 310 may be disposed in a top portion of handle(s) 101, so that a user may activate the keypad 310 with his or her thumb(s) without releasing his or her grip on the handles 101; display 308 may also be disposed in a top portion of handle(s) 101, near keypad 310. Optionally, a user may lock (or deactivate) keypad 310, so that keypad 310 is not accidentally activated while jumping; or keypad 310 may automatically be locked (or deactivated) by CPU 302 when it detects that the jump rope 100 is in use. In addition or in the alternative, keypad circuit 309 may be deactivated to prevent inadvertent commands from being acted upon by CPU 302 while the jump rope 100 is in use; or CPU 302 may simply ignore any commands it receives during that time.

Memory 303 may store digital information such as music or other audio files (e.g., .mp3 files) which may be transferred from a computer or other electronic device or which may be previously stored in memory 303. The audio files may be played back to a user through a headset (e.g., earphones) attached to a headset jack in one of handles 101. This embodiment is particularly useful because, while jumping rope, separate music players (e.g., smartphones) often come loose and fall to the ground. This problem is avoided by integrating the music player into the handle 101. Controls may also be integrated into keypad 310 disposed in the handle for starting/stopping the audio, selecting tracks, etc., as would be apparent to one of skill in the art in view of the present disclosure. Keypad 310 may be recessed into the handle 101 or locked while the jump rope 100 is in use in order to prevent inadvertent actuation of the controls.

In some embodiments, sensory output device(s) 312 may include one or more motors or vibration devices disposed inside one or both of handles 101 to give the user sensory feedback during his or her workout. For example, the handles 101 may vibrate when software running on CPU 302 determines that a certain goal has been reached, such as time, number of jumps, or calories burned. Alternatively or in addition, sensory output device(s) 312 may include a beeper, buzzer, or other audible device (such as a speaker or headset) for audibly informing a user when his or her goal has been reached. LEDs (or other lights) may also be used to provide visual feedback to the user, for example, by blinking a certain number of times when a goal is reached. Sensory feedback—audible, visual, or tactile—may also be used to inform users when they are off target, such as when they are jumping too slowly or without properly rotating the handles 101.

Sensors 311 may comprise one or more rotational sensors, which may use a magnetic field, reference marks, a reference gear (or wheel), variable resistance, or other means to detect the rotation (and/or rotational speed) of rope portion 102 relative to handle(s) 101. Alternatively or in addition, sensors 311 may include motion sensors to detect motion in handle(s) 101 and/or in rope portion 102. Alternatively or in addition, sensors 311 may detect vital statistics of the user, such as blood pressure and/or heart rate. For example, sensors 311 may include one or more electrodes disposed in the surface of one or both of handle(s) 101. The one or more electrodes may contact the user's skin and provide an output indicative of the user's heart rate, which heart rate may be monitored by CPU 302 and/or stored in memory 303. In some embodiments, two electrodes may be provided, one in each of handles 101; sensor circuitry may apply a predetermined voltage (e.g., constant, square wave, or other waveform) between the two electrodes and perform signal processing to detect a heart rate based on changes in the voltage. One of skill in the art, in view of the present disclosure, would understand that various rotational (or other) sensors may be used within the scope of the invention(s) in order to count the jumps, measure the resistance, and/or measure the rotational speed of the rope portion 102 relative to the handles 101.

In a preferred embodiment of the present disclosure, CPU 302 may determine from one or more sensors 311 when a user has started jumping rope (e.g., by detecting a predetermined number of consecutive rotations). CPU 302 may then begin counting the time, number of jumps, calories burned, and/or other target metric for the workout interval. When CPU 302 determines that a target has been reached (e.g., the time interval has elapsed), CPU 302 may activate one or more sensory output devices 312 to notify the user (e.g., the handle vibrates after 2 minutes of jumping rope). A user then knows that his or her target has been reached. This process can be repeated for multiple intervals during a workout. In this way, a user is freed from the burden of having to separately track his or her workouts, for example, by using a standalone timer, which is particularly difficult when jumping rope because the activity requires the use of both hands.

In other embodiments, handle(s) 101 may vibrate (or provide another sensory output) at various times, such as when it is time to start a first interval, when it is time to stop a first interval, at a predetermined time before a second interval, when it is time to start a second interval, and so on until the workout is complete. The vibration pattern (or other sensory output pattern) may vary to indicate which type of signal is being provided (e.g., start, stop, get ready, workout complete, etc.). A timer may be started at a time that coincides with a "start" pattern provided by sensory output device(s) 312; similarly, a timer may be stopped at a time that coincides with a "stop" pattern provided by sensory output device(s) 312. Alternatively, electronics 300 may wait to start a timer until detecting that the jump rope 100 is in use.

In an alternative embodiment, rather than CPU 302 automatically starting a timer, a user may press a button (or activate another input mechanism) in one of handles 101 to begin a workout interval. For example, a user may press a button in keypad 310 to start a timer (e.g., provided by CPU 302). When the timer expires, one or more of sensory output device(s) 312—audible, visual, or tactile—may be activated to notify the user.

Other hardware and/or software may be included in electronics 300 in order to realize the objectives of some embodiments of the present invention(s), as would be understood by a person of skill in the art in view of the present disclosure.

Handles 101 may be made of any suitable material, as would be understood by a person of skill in the art in view of the present disclosure. Such materials may include wood, steel, plastic, carbon fiber, aluminum, polyvinyl chloride, and/or a combination or hybrids of such materials. Handles 101 may be formed by injection molding, extrusion molding, blow molding, gas-assist molding, structural-foam molding, coinjection, reaction-injection molding, shaped thermoforming, rotational molding, casting, 3-D printing, carving, machining, or any other suitable process. Each handle 101 may be manufactured as a single piece or as multiple pieces fitted, glued, or otherwise held together. In addition, handles 101 may be configured to facilitate jumping rope, by, among other things, including grips and being formed in a shape that facilitates a user holding on to each handle 101 and maintaining his or her grip on handles 101 while jumping rope. Handles 101 may also be configured to allow a user to manipulate the rope portion 102 as necessary to jump rope effectively.

With reference to FIG. 1, handles 101 are shown as having a curved shape. For ease of reference bottom portion 106 refers to the portion of handle 101 closer to the center of the user's body when he or she is jump roping, and top portion 107 refers to the portion of handle 101 farther from the center of the user's body when he or she is jump roping. As illustrated, bottom portion 106 may be wider and generally uniform in shape, while top portion 107 may be more curved and flared out towards the top. This design helps a user to grip handle 101, and maintain his or her grip while jumping rope. Nonetheless, as would be recognized by a person of skill in view of the present disclosure, handles 101 may have any number of other shapes than that illustrated in FIG. 1, including a cylindrical shape having a roughly equal diameter throughout the handle 101, as illustrated in several figures herein.

In some embodiments, the surface of each handle 101 may include texturing that facilitates holding onto the handle 101. Such texturing may include, grooves or divots, or may include tape, leather, rubber, plastic, or other materials that increase the coefficient of friction between a user's hands and handles 101.

Handle 101 may include a channel 108. Channel 108 may extend the complete length of handle 101. Alternatively, channel 108 may extend less than the full length of handle 101. In some embodiments of the present disclosure, the ends of rope portion 102 of jump rope 100 may be disposed within channel 108 of each handle 101. Handle 101 may also include an opening for holding electronic circuit board 301 and electronics 300. Handle 101 may also include one or more openings for optionally providing access to a USB port, a headphone jack, display 308, and/or keypad 310.

Figure 2:
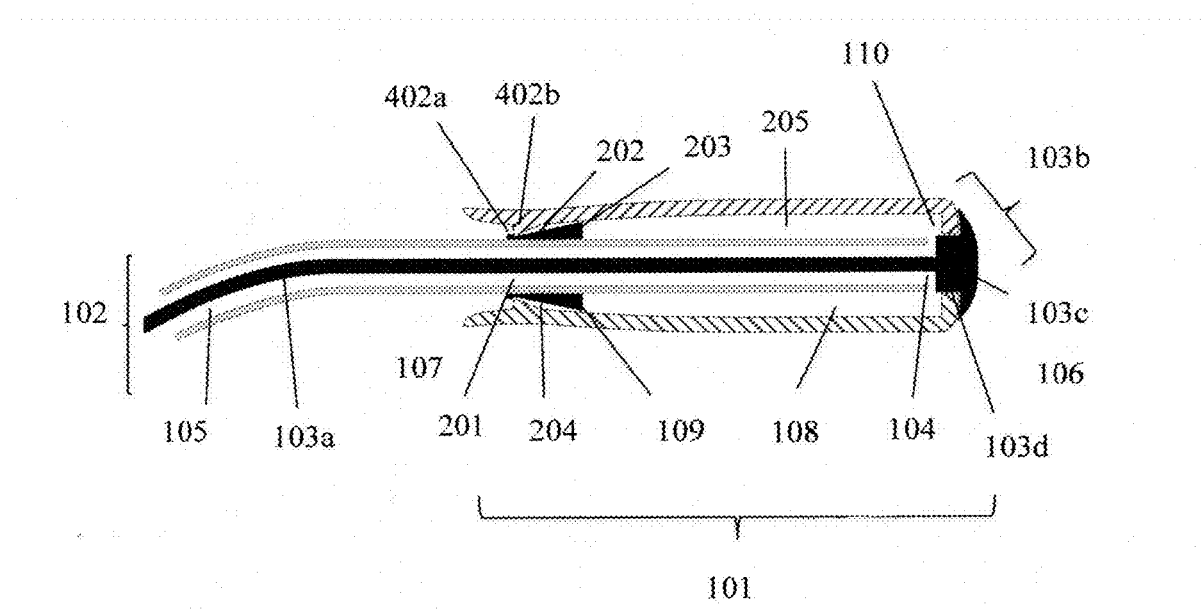
FIG. 2 shows an example of a handle connected to an end of the rope portion of a jump rope in accordance with aspects of the present disclosure.

Referring to FIG. 2, an example of a handle 101 connected to an end of rope portion 102, in accordance with aspects of the present disclosure, is shown. Handle 101 and rope portion 102 may be connected by first connector 109. For illustrative purposes, FIG. 2 shows first connecter 109 as a rubber grommet, but as would be understood by a person of skill in the art in view of the present disclosure, first connector 109 may be any other number of suitable devices, including, without limitation, a flanged eyelet, an adjustable screw, flange, or other similar devices, and may be made of any number of other suitable materials, such as metal, plastic, ceramic, or wood.

Figure 3:
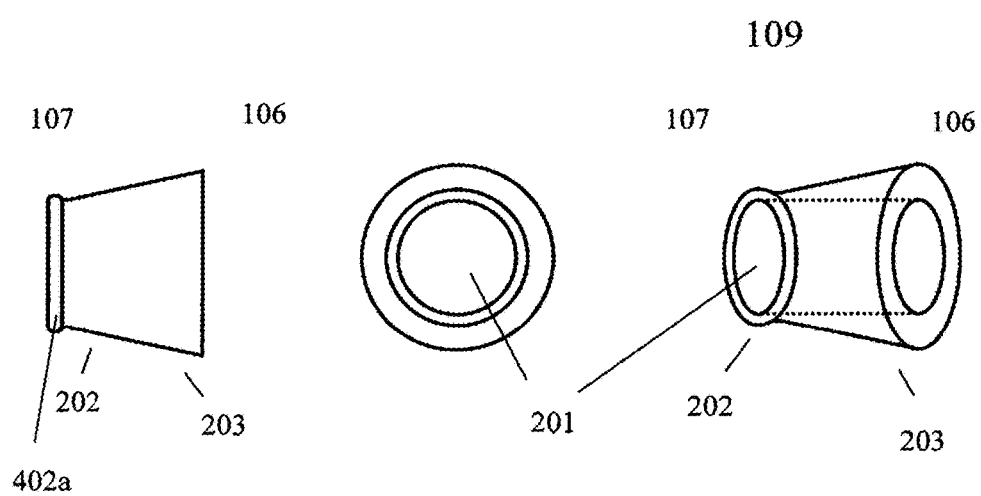
FIG. 3 shows various angles of an example of a connector that may be used with aspects of the present disclosure.

FIG. 3 shows various angles of an example of a first connector 109 in accordance with aspects of the present disclosure. First connector 109 may include a bore or channel 201 that extends the length of first connector 109. As illustrated in FIG. 2, the end of rope portion 102 may be disposed within or through bore 201. In some embodiments, first connector 109 may have a tapered end 202 and a flared end 203. Alternatively, first connector 109 may have a number of different shapes and configurations. For example, first connector 109 may have a uniform diameter throughout.

With reference to FIG. 2, channel 108 may include a tapered portion 204 at or near the top portion 107 of handle 101, and a non-tapered portion 205. First connector 109 may be disposed within channel 108, so that tapered end 202 of first connector 109 is closer to the top portion 107 of handle 101 than flared end 203.

First connector 109, and in turn rope portion 102, may be affixed to handle 101 by moving first connector 109 up channel 108 towards top portion 107 of handle 101 and into the tapered portion 204 of channel 108. When first connector 109 is outside of tapered portion 204, the end of rope portion 102 can be threaded through bore 201. Moving first connector 109 into tapered portion 204 exerts sufficient force against first connector 109 to, along with friction, fasten it to handle 101. Moreover, moving first connector 109 into tapered portion 204 also compresses bore 201, which in turn applies sufficient force to the portion of rope portion 102 threaded through bore 201 to affix rope portion 102 to handle 101. This design, along with other embodiments disclosed herein that allow the length of rope portion 102 outside of handle 101 to be increased or decreased, has the benefit of allowing the user to adjust the length of jump rope 100 to fit his or her height. This also has the added benefit of allowing multiple users of varying height (and skill level as discussed below) to share the same jump rope 100.

Notably, the length of jump rope 100 may vary depending on a user's skill level. In general, longer jump ropes require less skill and technique to use as compared to shorter jump ropes, because longer ropes have a greater margin for error. Accordingly, novice users may require a longer rope portion 102 to be disposed outside handles 101. Conversely, shorter ropes generally require better skill and technique to use properly, and more experienced users may require a shorter rope portion 102 be disposed outside handles 102. In some embodiments, a user may progressively decrease the length of jump rope 100 as he or she develops the proper jump roping technique and skills, and thus, progressively increase the challenge of jumping rope.

Figures 4A, 4B:
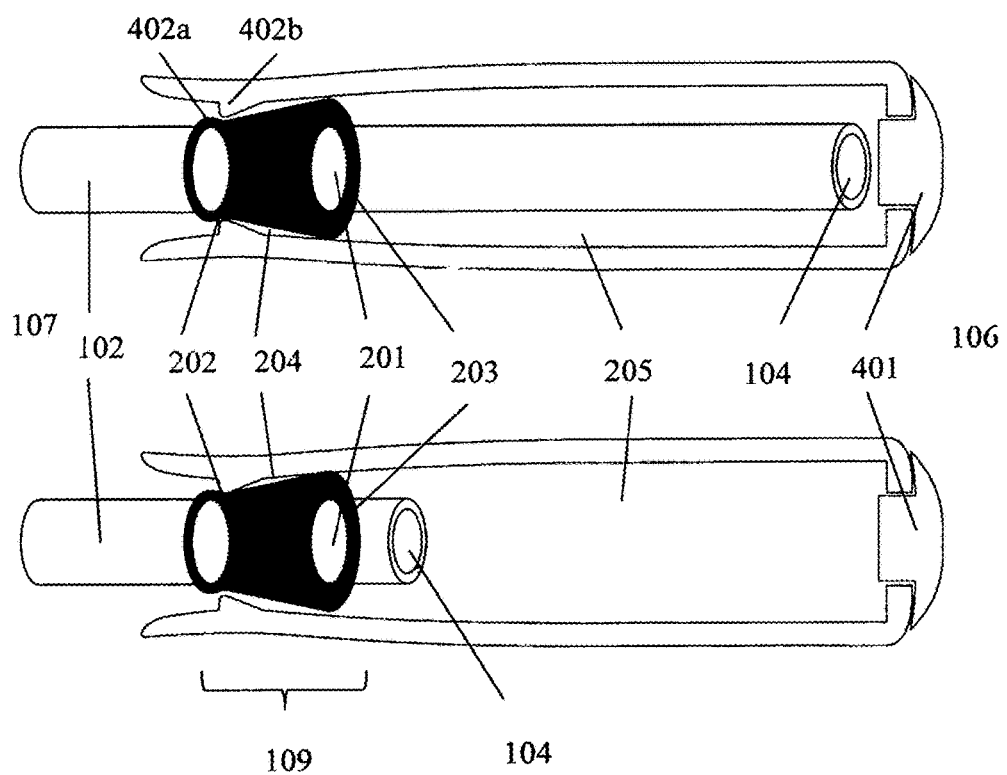
FIGS. 4a and 4b show an example of a handle with an adjustable-length rope portion in accordance with aspects of the present disclosure.

FIGS. 4a and 4b show an example of a handle 101 with an adjustable-length rope portion 102 in accordance with aspects of the present disclosure. With reference to FIG. 4a, the end of rope portion 102 is threaded through bore 201 of first connector 109, so that the end of rope portion 102 spans the entire length, or nearly the entire length, of channel 108.

As shown in FIG. 4b, a user may increase the amount of rope portion 102 disposed outside of handle 101, and thus increase the length of jump rope 100, by adjusting the position of rope portion 102 in relation to first connector 109. In this respect, the length of the rope portion 109 disposed outside of handle 101 may be increased (or decreased) by the length of, or nearly the length of, handle 101. In addition, by implementing this design in both handles 101, the length of the jump rope 100 may be increased (or decreased) by the combined length of, or nearly the combined length of, both handles 101.

The above can be achieved by moving first connector 109 out of tapered portion 204 of channel 108. This may be achieved by, among other things, angling top portion 107 of handle 101 up, while pushing rope portion 102 towards the bottom portion 106 of handle 101. This allows the force of gravity to assist in moving and maintaining first connector 109 out of tapered portion 204 of channel 108. When first connector 109 is moved out of the tapered portion 204, bore 201 returns to its uncompressed size, which allows rope portion 102 to be moved relative to first connector 109. In some embodiments, bottom cap 401 may be removed from handle 101. This allows rope portion 102 and first connector 109 to be moved out of handle 101 through the bottom portion 106 as needed to adjust the length of rope portion 102 disposed outside of handle 101.

Once the portion of rope portion 102 disposed outside of handle 101 has been adjusted to the desired length, rope portion 102 may be secured to handle 101 by moving first connector 109 back into tapered portion 204 of channel 108. This may be achieved by, among other things, angling top portion 107 of handle 101 down, while pulling rope portion 102 towards top portion 204 of handle 101 and into the tapered portion 204 of channel 108. A user may remove bottom cap 401 in order to access first connecter 109, and may then, to the extent necessary, push first connector 109 into tapered portion 204 of channel 108.

First connector 109 and channel 108 may also each have a lip 402a and 402b, respectively. Lips 402a and 402b may interlock, or otherwise connect, as first connector 109 moves into tapered portion 204, and, in this way, first connector 109 may be secured to handle 101. As will be apparent to a person of skill in the art in view of the present disclosure, various other mechanisms may be employed to secure first connector 109 to handle 101.

In another embodiment (which is not illustrated), channel 108 need not have a tapered portion 204, and instead a cap having a bore, through which rope portion 102 is disposed, may be used to compress first connector 109 and, thus, affix rope portion 102 to handle 101. The cap may be positioned within handle 101 next to first connector 109, so that the cap is closer to top portion 107 of handle 101 than first connector 109. The cap may include a recess that allows first connector 109 to be inserted into the cap. The cap's recess may be tapered, or may utilize some other mechanism to compress first connector 109, and thus secure rope portion 102 to first connector 109. When a user desires to adjust the length of the jump rope 100, he or she may remove bottom cap 401, and thus access the cap and first connector 109. A user may then remove first connector 109 from the cap, alleviating the compressive force on first connector 109 and allowing bore 201 to return to its uncompressed size. This, as previously described, loosens the grip of first connector 109 on rope portion 102 allowing rope portion 102 to be adjusted relative to first connector 109.

Figure 5:
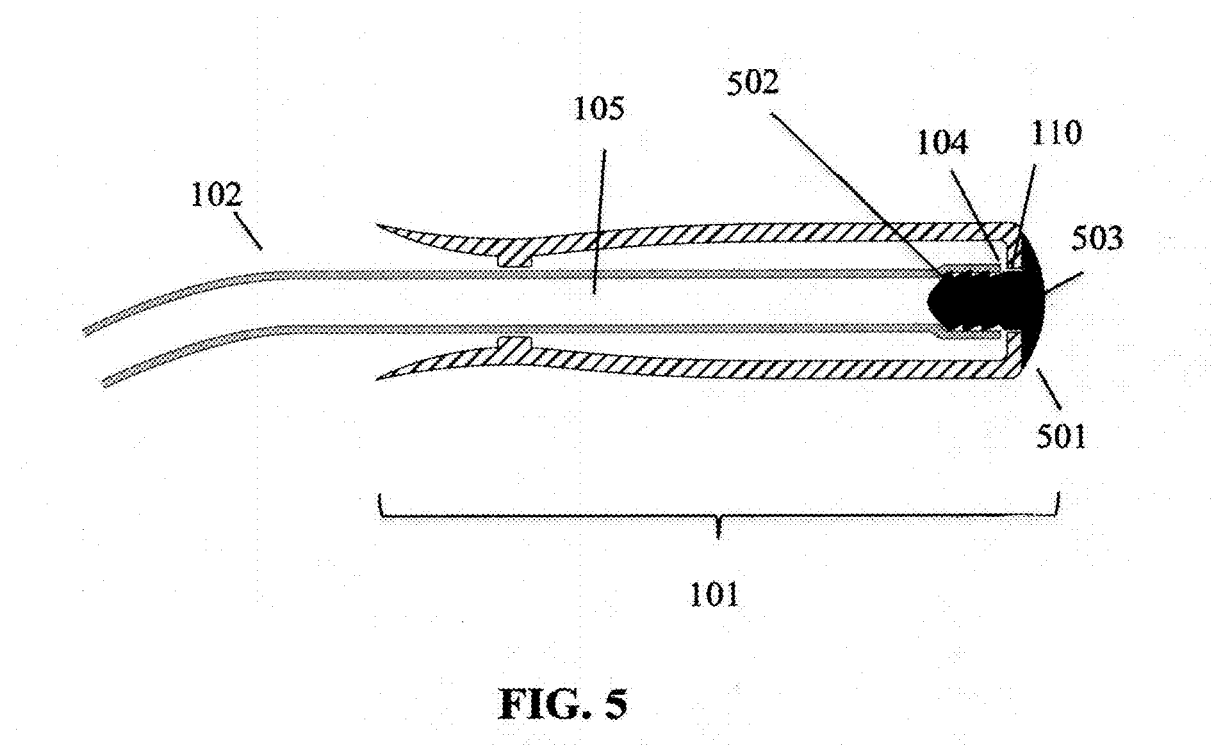
FIG. 5 shows an example of a handle with a second connector in accordance with aspects of the present disclosure.

FIG. 5 shows an example of handle 101, in accordance with another aspect of the present disclosure, which includes second connector 501. In this embodiment, the end of rope portion 102 may be disposed within channel 108, and may span the entire length, or nearly the entire length, of handle 101. Rope portion 102 may be affixed to handle 101 by inserting narrow portion 502 of second connector 501 into opening 104.

For illustrative purposes, FIG. 5 shows second connecter 501 as comprising a rivet screw, but as would be understood by a person of skill in the art in view of the present disclosure, second connector 501 may comprise any other number of suitable devices, including a rivet, screw, or similar connector or fastener having a T or tapered shape.

Narrow portion 502 may include a screw, or may have helical threads or grooves on its surface, and may be screwed into opening 104, thus affixing rope portion 102 to handle 101. In such an embodiment, opening 104 may include complimentary threads or grooves for receiving narrow portion 502. Alternatively, if rope portion 102 is made of plastics, rubbers, elastomers, and/or any hybrid of such materials having a durometer between Shore 65 and Shore 85, such materials may conform to the screw-shape of narrow portion 502, effectively forming complimentary threads or grooves for receiving narrow portion 502.

In some embodiments, narrow portion 502 may have a slightly larger diameter than opening 104. If rope portion 102 is made of an elastic material, second connector 501 may be inserted into opening 104, and held in place by the compressive force exerted on narrow portion 502 by rope portion 102, which in turn affixes rope portion 102 to handle 101. In yet another embodiment, an adhesive, bonding agent or similar material may be used to hold narrow portion 502 within opening 104 of rope portion 102.

As would be understood by a person of skill in the art in view of the present disclosure, jump rope 100 may utilize both first connector 109 and second connector 501, or alternatively, may utilize only one, or none, of first connector 109 and second connector 501.

Figure 15:
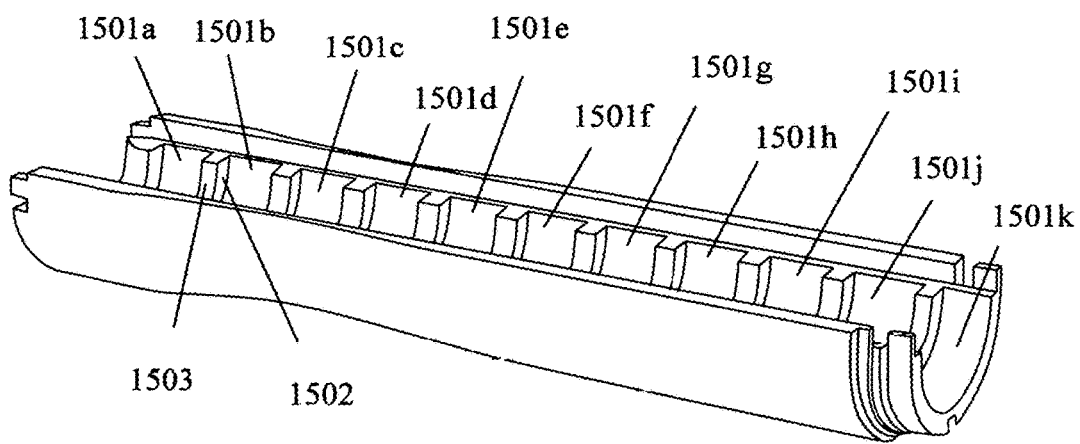
FIG. 15 shows a cross section of an example of a handle with an adjustable-length rope portion in accordance with aspects of the present disclosure.

FIG. 15 shows a cross section of a handle 101 with an adjustable-length rope portion 102 in accordance with embodiments of the present disclosure. In this embodiment, channel 108 comprises a plurality of chambers 1501, wherein each chamber 1501 is separated from an adjacent chamber by a divider 1502. The length of jump rope 100 may be adjusted (increased or decreased) by securing second connector 501 within a chamber 1501 corresponding to a desired length of rope portion 102 to be disposed outside of handle 101. Moreover, because dividers 1502 may be evenly spaced (e.g., every half inch) in some embodiments, a user may know precisely how much adjustment is being made to the length of jump rope 100, advantageously allowing the user to quickly and precisely change the length of jump rope 100. In some embodiments, markings may be included indicating the length and/or spacing of each divider 1502 (e.g., every half inch). Thus, a user may adjust the length of jump rope 100 by affixing rope portion 102 to second connector 501 and placing second connector 501 within a chamber 1501 corresponding to a desired length of jump rope 100. Alternatively, second connector 501 may already be affixed to rope portion 102, either permanently (e.g., with an adhesive) or removably.

Figure 17:
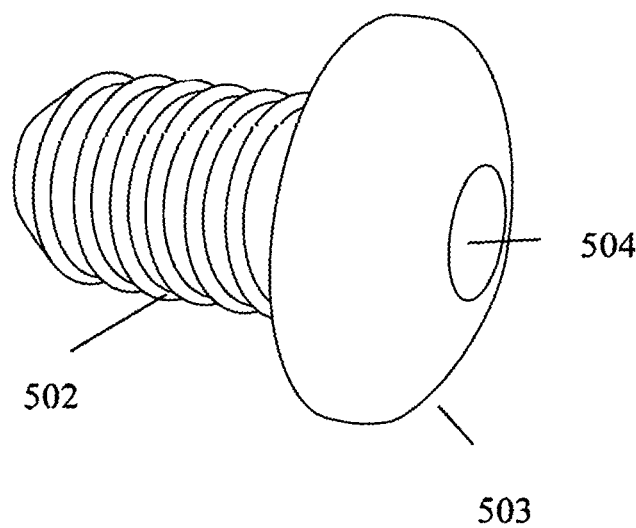
FIG. 17 shows an example of a connector in accordance with aspects of the present disclosure.

As shown in FIG. 17, second connector 501 may comprise narrow portion 502 and wide portion 503. In some embodiments, wide portion 503 may fit within chamber 1501, and may be shaped such that second connector 501 (and rope portion 102) may rotate freely within chamber 1501, but, nonetheless, may not pass through divider 1502 into an adjacent chamber. Moreover, when jump rope 100 is in use, centripetal force may press wide portion 503 into a surface of divider 1502; friction between wide portion 503 and divider 1502 may create rotational resistance. The surface texture(s) and amount of surface area of wide portion 503 contacting divider 1502 may be varied, as a design choice, in order to control the amount of friction. In this way, greater rotational resistance may be provided than in conventional jump rope devices.

Figure 18:
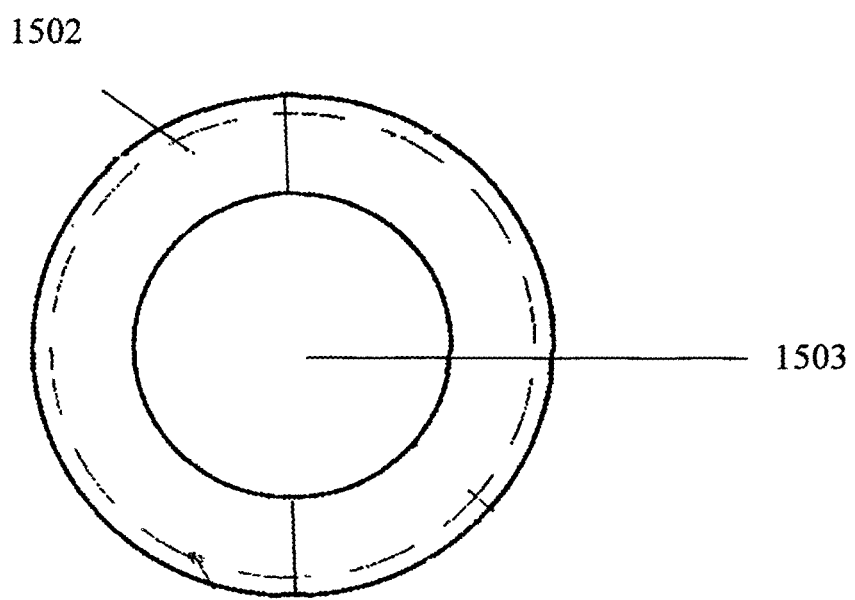
FIG. 18 shows a top view of an example of a divider in accordance with aspects of the present disclosure.

FIG. 18 shows an example of a top view of a divider 1502 in accordance with an aspect of the present disclosure. Divider 1502 may comprise a flat-faced flange having an opening 1503. Second connector 501 (or a similar connector with a T or tapered shape) may be affixed to rope portion 102 as described herein, and then placed within a chamber 1501 corresponding to a desired length of jump rope 100. Opening 1503 may have a diameter larger than the outer diameter of rope portion 102, but smaller than wider portion 503 of second connector 501. In this way, rope portion 102 may pass through opening 1503 (and divider 1502), but second connector 501 may be prevented from passing completely through opening 1503, thus securing second connector 501 within chamber 1501.

Second connector 501 (or any similar connector) may also include a bore or aperture 504 that runs the length of second connector 501 through which weighted core 103 may be inserted into rope portion 102. Weighted core 103 may be wider, or have a greater diameter, at its end than bore or aperture 504. This may prevent weighted core 103 from slipping completely into rope portion 102, and may provide a grip or handle by which a user can remove weighted core 103 from second connector 501 (and thus from rope portion 102).

In one preferred embodiment, opening 1503 has a diameter at least 0.25 inches larger than the outer diameter of rope portion 102. And in yet another preferred embodiment, opening 1503 has a diameter at least 0.5 inches smaller than wider portion 503 of second connector 501. Thus, assuming the outer diameter of rope portion 102 is 0.5 inches, opening 1503 may have a diameter of 0.75 inches, while the wider portion of second connector 501 may have a diameter of 1.25 inches. In this way, the size of opening 1503 is sufficiently large so as to allow rope portion 102 to be disposed through it, but sufficiently small to prevent wide portion 503 of second connector 501 from passing through opening 1503.

Notwithstanding the foregoing, as would be understood by a person of ordinary skill in the art in view of the present disclosure, opening 1503 may be any diameter that allows rope portion 102 to pass through divider 1502, while preventing second connector 501 from completely exiting chamber 1501, so long as rope portion 102 is not prevented from functioning as the rope portion of jump rope 100 and handle 101 maintains such size and dimensions so as to be able to function as the handle portion of jump rope 100. Moreover, despite references herein to the diameter of opening 1503, opening 1503 is not intended to be limited to a particular shape, and may comprise any number of non-circular shapes.

As further illustrated in FIG. 15, in one embodiment channel 108 may comprise 11 chambers 1501 (chambers 1501a through 1501k) separated by 10 equally spaced dividers 1502. Each divider 1502 may be spaced approximately ½ an inch apart from the next divider 1502. This allows the length of jump rope 100 to be adjusted in ½ inch increments by a total of 5 inches per handle 101.

The length of rope portion 102 outside handle 101 may be maximally extended by securing second connector 501, once it is affixed to rope portion 102, within chamber 1501a (the chamber closest to top portion 107). In such an embodiment, second connector 501 may be placed within the desired chamber 1501 with narrow portion 502 (and thus rope portion 102) facing towards top portion 107. The length of rope portion 102 outside handle 101 may be subsequently shortened from its maximal length by securing second connector 501 within a subsequent chamber 1501 corresponding to a desired length of jump rope 100. For example, to shorten the length of rope portion 102 outside handle 101 by an inch second connector 501 may be moved from chamber 1501a to chamber 1501c. To adjust rope portion 102 to its shortest length outside handle 101 second connector 501 may be secured within chamber 1501k (the chamber closest to bottom portion 106). In this way, by utilizing two handles 101 in accordance with this embodiment, the length of rope portion 102 disposed outside each handle 101 (or the length of jump rope 100) may be adjusted by up to 10 inches in ½ inch increments.

While for illustrative purposes FIG. 15 shows channel 108 as comprising 11 chambers 1501 and 10 dividers 1502, channel 108 may comprise more or fewer chambers 1501 than illustrated, and may include more or fewer dividers 1502. As would be understood by a person of skill in view of the present disclosure, channel 108 may comprise any number of chambers 1501, and include any number of dividers 1502, so long as each chamber 1501 maintains the necessary dimensions (e.g., height, length, and width) to allow second connector 501 (and rope portion 102) to rotate within chamber 1501.

In addition, dividers 1502 need not be evenly spaced throughout channel 108. For example, in some embodiments dividers 1502 located closer to top portion 107 may be spaced farther apart than dividers 1502 closer to bottom portion 106, or vice versa.

In accordance with the present embodiments, handle 101 may also be configured to enable a user to access chambers 1501, and thus locate and secure second connector 501 within a chamber 1501 corresponding to a desired length of jump rope 100. For example, with reference to FIG. 16, handle 101 may comprise several parts or portions—a male portion 1604, a female portion 1605, and cap portion 1606—that may be reversibly fastened or connected to one another in order to allow a user to open handle 101 and access channel 108.

Male portion 1604 may be fastened to female portion 1605 using one or more fastening mechanisms, so as to enable male portion 1604 and female portion 1605 to be separated from each other and subsequently refastened. Once male portion 1604 and female portion 1605 are separated, a user may access channel 108 and place second connector 501 in a chamber 1501 corresponding to a desired length of rope portion 102 to be disposed outside handle 101.

Figure 16:
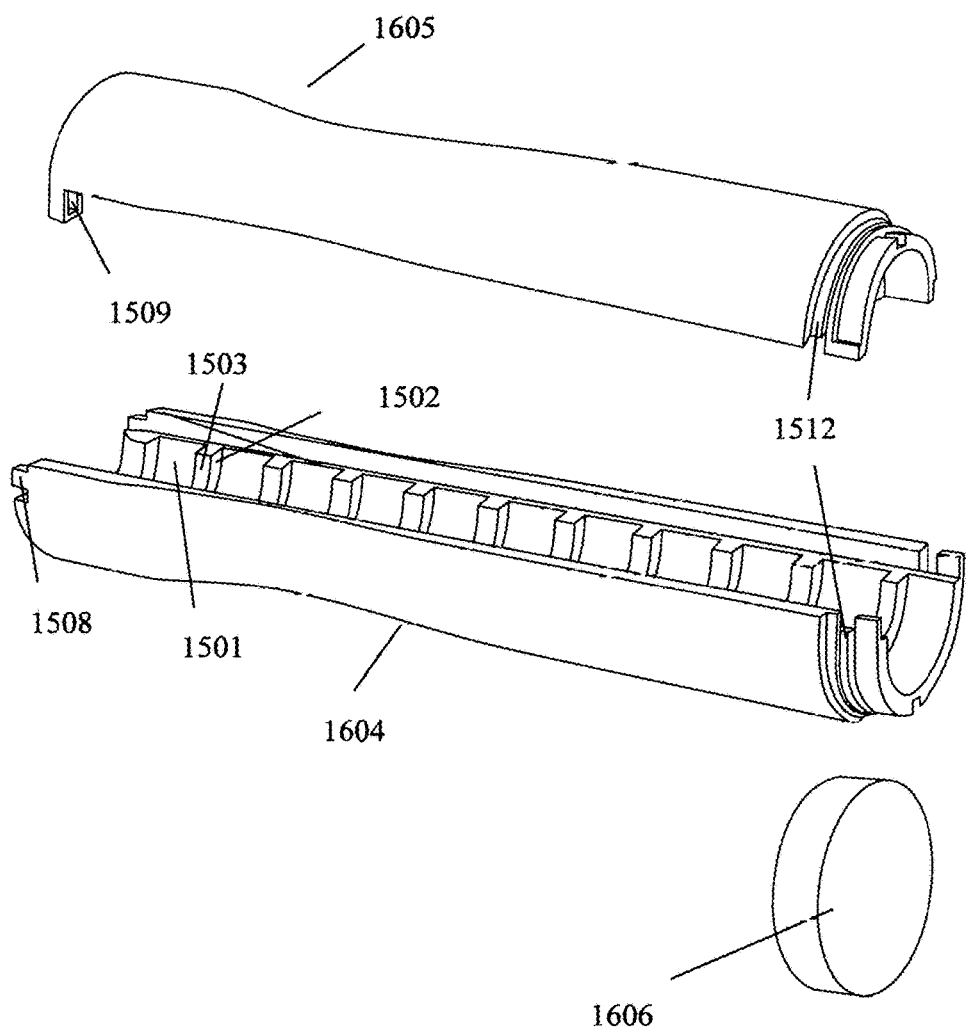
FIG. 16 shows an example of handle with an adjustable-length rope portion comprising a plurality of parts reversibly connected to one another in accordance with aspects of the present disclosure.

As illustrated in FIG. 16, divider 1502 and opening 1503 may be split or divided between male portion 1604 and female portion 1605. When male portion 1604 and female portion 1605 are fastened both halves of divider 1502 may be connected, thus forming opening 1503. This prevents connector 501 from moving into an adjacent chamber 1501 as described herein, and thus secures second connector 501 (and the end of rope portion 102) within a chamber 1501.

Male portion 1604 and female portion 1605 may be reversibly fastened or connected using any number of suitable mechanisms, including pins, retaining rings, snap fastener, threaded fasteners, latches, screws, etc. For example, male portion 1604 may include pins 1508, which may be inserted into corresponding apertures 1509 on female portion 1505 to reversibly fasten male portion 1604 and female portion 1605 along the top portion 107 of handle 101. Once pins 1508 are inserted into apertures 1509, cap portion 1606 may be reversibly fastened to the opposing ends (ends opposite pins 1508 and apertures 1509) of male portion 1604 and female portion 1605. This may be accomplished by screwing or threading cap portion 1606 or (a portion of cap portion 1606) over male portion 1604 and female portion 1605 using channel 1512, which runs through both male portion 1604 and female portion 1605. Again, any number of other suitable mechanisms, including pins, retaining rings, snap fastener, different threaded fasteners, latches, etc., may be used to fasten cap portion 1606 to male portion 1604 and female portion 1605.

In some embodiments, male portion 1604 may be detached from female portion 1605 by unscrewing or unthreading cap portion 1606, and removing cap portion 1606. Pins 1508 may then be removed from their respective apertures 1509, allowing male portion 1604 to be separated from female portion 1605. By separating male portion 1604 from female portion 1605, a user may access channel 108, and thus place second connector 501 within a chamber 1501 corresponding to a desired length of rope portion 102 to be disposed outside of handle 101. By refastening male portion 1604 to female portion 1605, second connector 501 is secured within the chamber 1501 where it is located as described herein.

As would be recognized by a person of skill in the art in view of the present disclosure, handle 101 need not comprise a male portion 1604, female portion 1605, and cap portion 1606. For example, in some embodiments, handle 101 may comprise a single piece, wherein one lateral or side portion of handle 101 includes a hinge or movable joint, while the opposite side includes a connecting or fastening mechanism. In this embodiment, a user may unfasten the connecting or fastening mechanism (e.g., latch, pin, etc.) allowing the hinge to move and handle 101 to be opened. In this way, a user can access channel 108, and place second connector 501 in a desired chamber 1501. By refastening the connecting mechanism, second connector 501 may be secured within chamber 1501. Alternatively, handle 101 may comprise any number of parts or pieces. Such pieces may be identical to one another, or may differ from one another. Moreover, handle 101 may utilize any of a number of reversible connecting mechanisms or fasteners (e.g., pins, retaining rings, snap fastener, threaded fastener, latch, etc.).

Figure 13:
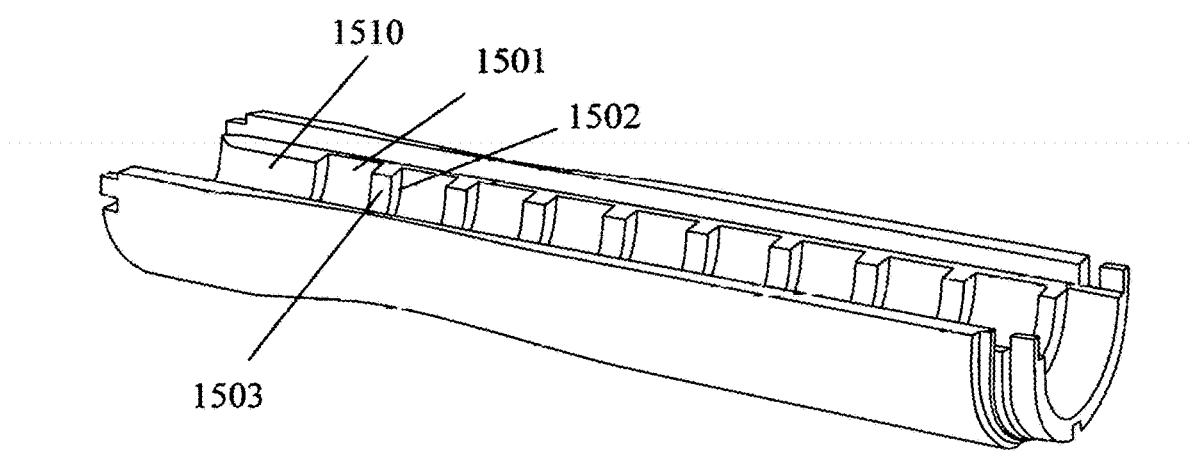
FIG. 13 shows a cross section of an example of handle with an adjustable-length rope portion in accordance with aspects of the present disclosure.

Rope portion 102 may have a tendency to strike or rub against channel 108 at or near top portion 107, which may wear rope portion 102 at the point of contact. As illustrated in FIG. 13, channel 108 may include a protective portion 1510 at or near top portion 107 of handle 101. Protective portion 1510 may help mitigate wear to rope portion 102 by increasing the contact area between channel 108 and rope portion 102 at or near top portion 107. Protective portion 1510 may also be made of, or be covered by, a material having a low coefficient of friction, which may further mitigate wear to rope portion 102.

In the present embodiments, when jump rope 100 is in use the end of rope portion 102 and second connector 501 rotate within the chamber 1501 housing second connector 501 and about the divider 1502 closer to top portion 107 of said chamber 1501 (except in the case of the top chamber 1501a, where the second connector 501 may rotate about the opening at the top portion 107 of the handle 101). The force produced while jumping with jump rope 100 forces second connector 501 against the top divider 1502. Dividers 1502 may be strengthened to deal with such forces by adding a strengthening mechanism, such as a brace or bracket (e.g., an L-brace), where the top of divider 1502 (the portion closest to top portion 107) connects to channel 108. Alternatively, instead of comprising a flat-faced flange, divider 1502 may comprise a raised-face or sloped-faced flange, wherein the top of divider 1502 is wider where it connects to channel 108 and narrows or tapers towards opening 1503.

In some embodiments of the present disclosure, a weighted core 103 (or multiple weighted cores 103) may be inserted into, and disposed within, hollow portion 105 of rope portion 102 of jump rope 100. Weighted core 103 may span the complete length of rope portion 102. Alternatively, weighted core 103 may span less than the complete length of rope portion 102.

Weighted core 103, when inserted into rope portion 102, preferably distributes weight evenly, or roughly evenly, throughout rope portion 102 of jump rope 100. Because weighted core 103 distributes weight evenly, or roughly evenly, throughout rope portion 102, rotation of jump rope 100 remains balanced, which supports a smooth, even and natural jump roping experience.

In some embodiments, two weighted cores 103, each roughly spanning half the length of rope portion 102, may be inserted into opposite ends of rope portion 102, and simultaneously disposed within rope portion 102. Preferably, the two weighted cores 103 are roughly the same length, weight, and proportions so as to, when disposed within rope portion 102, evenly distribute weight throughout rope portion 102.

Weighted cores 103 of varying weight and material may be inserted into rope portion 102. By varying the weight of weighted core 103, a user can increase (or decrease) the weight of rope portion 102. In this way, a user may progressively increase the rotational resistance of rope portion 102, and thus increase the difficulty of the exercise. Over time, such progressive increases lead to increases in strength and endurance. Moreover, because weight is evenly distributed throughout rope portion 102, or roughly evenly distributed, a user is able to increase resistance, while maintaining a smooth rotation of jump rope 100.

Weighted core 103 may be comprised of any material sufficiently flexible and durable to be inserted into rope portion 102 and allow rope portion 102 to be used to jump rope. Such materials may include, without limitation, plastics, rubber, elastomers, any hybrid of such materials, braided steal, metal chain, pro-vinyl, leather, nylon, cable, vinyl coated steel, or any other sufficiently flexible and durable material as will be apparent to those skilled in the relevant art after reading the present disclosure. In some embodiments, weighted core 103, may be a hollow plastic and/or rubber cord or tube weighing approximately 1 to 1.5 oz. In other embodiments, weighted core 103 may be a solid plastic and/or rubber cord weighing approximately 2 oz. And in yet other embodiments, weighted core 103 may be a steel cord, chain, or rope weighing approximately 3 oz. to 6 oz. Moreover, a user may optionally switch between different weighted cores 103 to achieve different jumping effects.

Referring again to FIG. 2, weighted core 103 may comprise a single unit, or alternatively multiple units, having a T or tapered shape with an extended portion 103a and a stopper portion 103b. The extended portion 103a may extend the length of rope portion 102 (or half the length in the case of two weighted cores 103), and may be inserted into rope portion 102 via opening 104 and handle opening 110 of handle 101.

Stopper portion 103b may include wider portion 103c having a larger width or diameter than handle opening 110, and smaller portion 103d that may be inserted into handle opening 110. Smaller portion 103d of stopper portion 103b may have a width or diameter roughly equal to, or slightly smaller than, the width or diameter of handle opening 110, or, alternatively, smaller portion 103*d* may have a width or diameter slightly larger than handle opening 110.

In some embodiments, smaller portion 103*d* may comprise a screw. Handle opening 110 may include complimentary threads or grooves capable of receiving smaller portion 103*d*, thus allowing smaller portion 103*d* to be screwed into handle opening 110. In such an embodiment, a user may secure weighted core 103 to handle 101 by inserting extended portion 103*a* of weighted core 103 into handle 101 and rope portion 102, and screwing smaller portion 103*d* of weighted core 103 into handle opening 110. A user may subsequently remove weighted core 103 by unscrewing smaller portion 103*d*, and removing weighted core 103 from rope portion 102 and handle 101.

In another embodiment, smaller portion 103*d* may be elastic, or otherwise made of a material that retains its shape after being compressed. Smaller portion 103*d* may have a width or diameter equal to, or slightly larger than, handle opening 110. A user may affix weighted core 103 to handle 101 by pushing smaller portion 103*d* into handle opening 110. This, in turn, causes weighted core 103 to be held in place by the compressive force applied by handle opening 110 to the smaller portion 103*d*. A user may remove weighted core 103 by pulling stopper portion 103*b* from handle opening 110.

In some embodiments, weighted core 103 may be affixed to the end of rope portion 102. In one such embodiment, the end of rope portion 102 may be disposed within channel 108, and may span the entire length, or may span the majority of the length, of handle 101. The smaller portion 103*d* of weighted core 103 may be inserted into handle opening 110, and pass through to channel 108, where smaller portion 103*d* may be inserted into hollow portion 105 through opening 104. Weighted core 103 may connect to rope portion 102 in the same manner as described with reference to second connector 501, and thus may serve the function of second connector 501, and secure rope portion 102 to handle 101. For example, in some embodiments smaller portion 103*d* may comprise a screw, and may thus be screwed into opening 104 of weighted core 103, as already described.

In some embodiments, smaller portion 103*d* may have a width or diameter equal to or greater than opening 104 and hollow portion 105. Smaller portion 103*d* may thus be inserted into opening 104, and affixed to rope portion 102 by the compressive force asserted on it by rope portion 102.

The wider portion 103*c* may have a diameter larger than handle opening 110. Thus, when rope portion 102 is connected to smaller portion 103*d*, stopper portion 103*b* affixes rope portion 102 to handle 101, and prevents the rope portion 102 disposed within the handle 101 from exiting the handle 101. Conversely, a user may remove rope portion 102 from handle 101 by removing weighted core 103.

In another embodiment, which utilizes second connector 501, extended portion 103*a* of weighted core 103 may be inserted into rope portion 102 via a bore or aperture 1504 in second connector 501. Bore or aperture 1504 may be of such size and/or shape as to prevent stopper portion 103*b* from entering it. In this way, weighted core 103 is prevented from falling completely into rope portion 102, and a user is able to remove weighted core 103 from rope portion 102 without removing second connector 501. This may be accomplished by simply pulling weighted core 103 out of second connector 501 using the stopper portion 103*b*. One advantage of this embodiment is that it allows weighted core 103 to spin independently of second connector 501, and thus facilitates the smooth and natural rotation of the jump rope 100. Notably, in such an embodiment, weighted core 103 may comprise any number of T or tapered-shape designs, and need not include smaller portion 103*d*.

Figure 6:
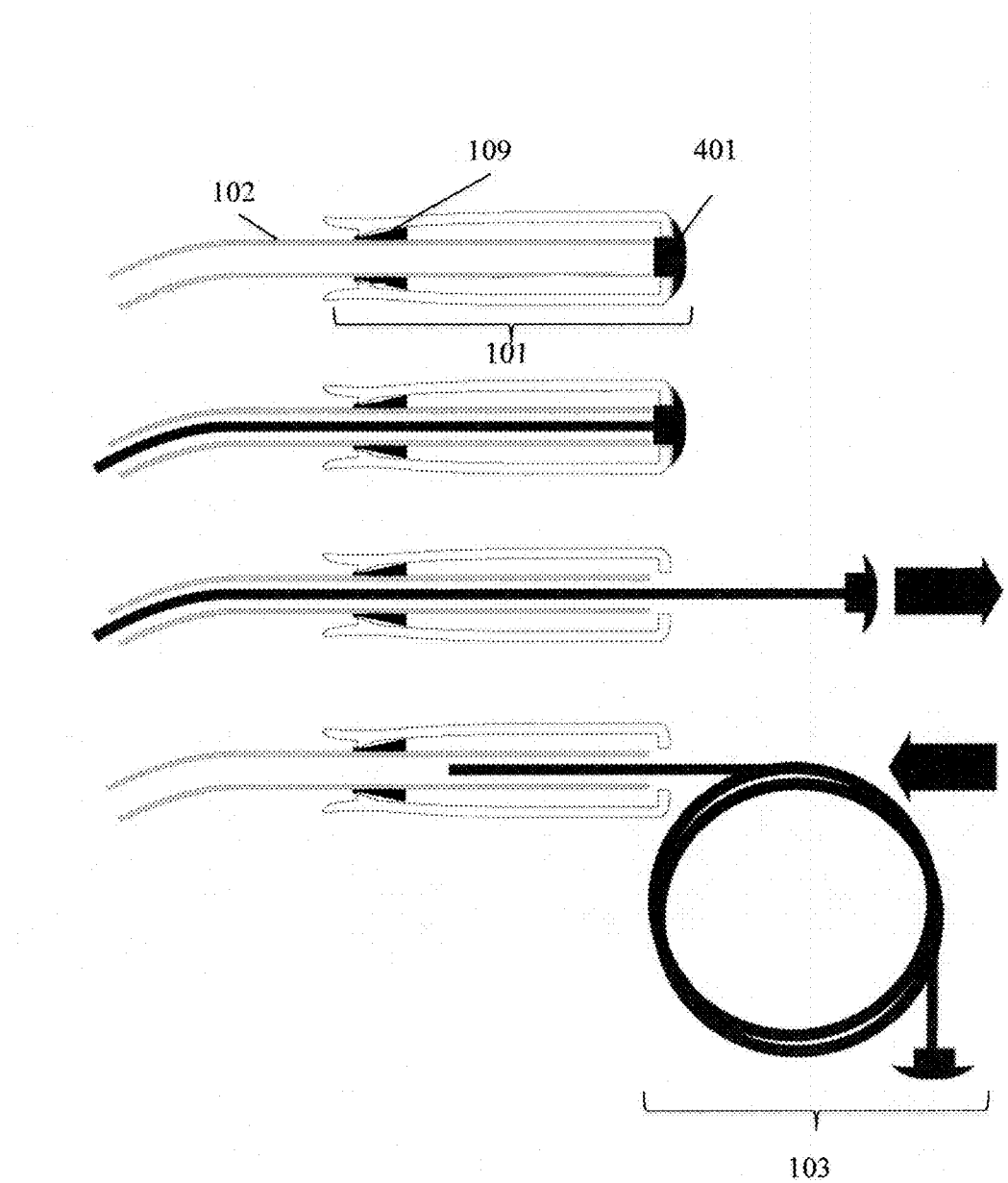
FIG. 6 shows an example of a handle, rope portion, and weighted core, in accordance with aspects of the present disclosure.

FIG. 6 shows an example of a handle 101, rope portion 102, and weighted core 103, in accordance with some embodiments of the present disclosure, and illustrates how weighted core 103 may be removed from, and inserted into, rope portion 102 and handle 101.

Figure 7:
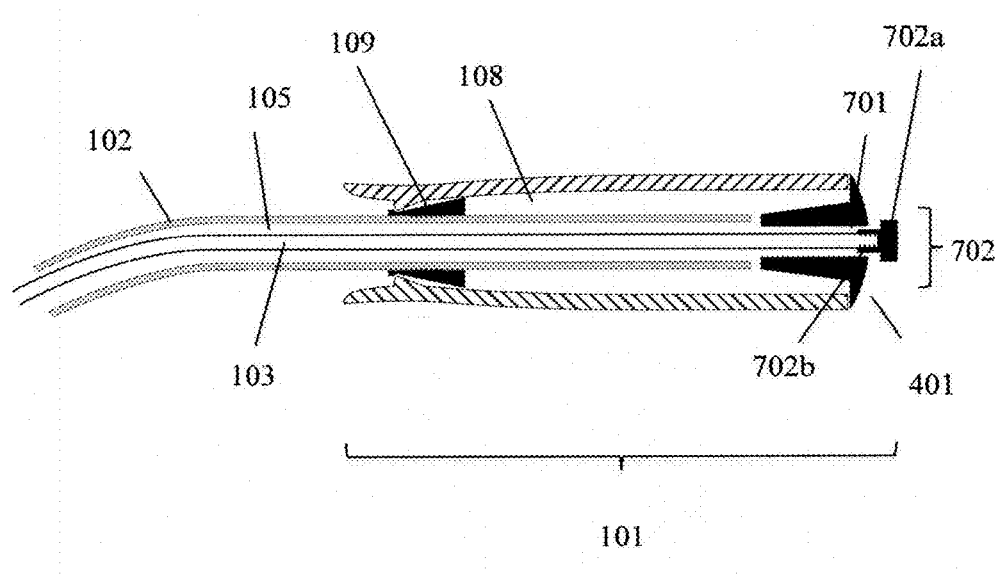
FIG. 7 shows an example of a weighted core in accordance with aspects of the present disclosure.

With reference to FIG. 7, an example of a weighted core 103 in accordance with some embodiments of the present disclosure is shown. As illustrated in FIG. 7, bottom cap 401 may have a bore or aperture 701 through which weighted core 103 may be inserted. In this embodiment, the extended portion 103*a* of weighted core 103 may be inserted or threaded through aperture 701, and weighted core 103 may be secured to bottom cap 401 by stopper portion 702. Stopper portion 702 may have a T or tapered shaped, and may include a wider portion 702*a* having a width or diameter greater than aperture 701, and a smaller portion 702*b* that may be disposed within aperture 701, and which may affix weighted core 103 to bottom cap 401. Smaller portion 702*b* is depicted as having helical threads or grooves, akin to a screw, which allows weighted core 103 to be secured to bottom cap 401 by screwing smaller portion 702*b* to aperture 701. But, as described herein and as would be understood by a person of skill in the art in view of the present disclosure, weighted core 103 may be secured to bottom cap 401 in a variety of ways (including in such ways as to allow weighted core 103 to rotate independently of rope portion 102 and/or handle 101).

In some embodiments, stopper portions 103*b* and 702 may be configured to facilitate adding and removing weighted core 103 from handle 101 and rope portion 102. For example, wider portions 103*c* and 702*a* may include a grip, such as a cross shaped groove, or alternatively, a divot having raised grooves, that allow a user to turn weighted core 103 (and if necessary unscrew weighted core 103 from handle 101 or bottom cap 401), and pull weighted core 103 from rope portion 102 and handle 101. Alternatively, weighted core 103 may have any number of designs, as would be apparent to a person of ordinary skill in view of the present disclosure, that facilitate adding and removing weighted core 103.

Figure 11:
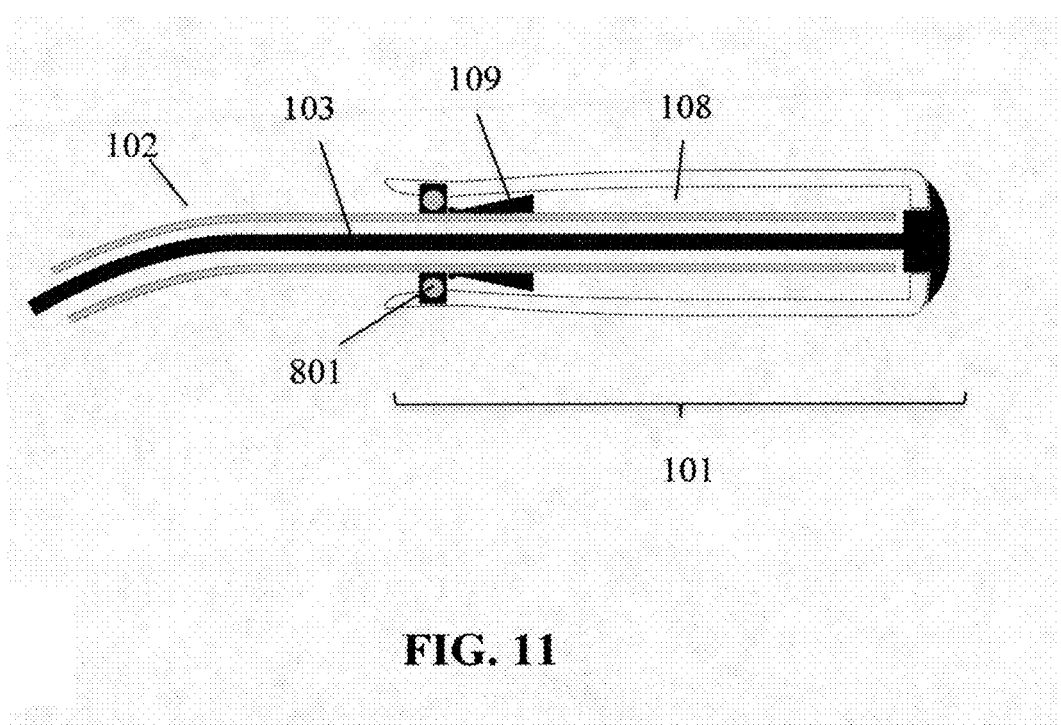
FIG. 11 shows an example of a handle in accordance with aspects of the present disclosure, which includes a bearing and internal connector.

FIG. 11 shows an example of a handle 101 that includes a bearing 801, in accordance with embodiments of the present disclosure. As illustrated, handle 101 may include a bearing 801 disposed at or near top portion 107 of handle 101. Bearing 801 may facilitate rotation of the rope portion 102 about the axis of handle 101, thus making it easier for a user to rotate jump rope 100.

While embodiments of jump rope 100 may utilize a ball bearing to facilitate rotation of rope portion 102 about the axis of handles 101, using a ball bearing may reduce the resistive force required to rotate rope portion 102 and make rotation easier, which provides less of an upper body workout. Therefore, in some embodiments, jump rope 100 does not use a ball bearing; rather, rope portion 102 rotates within handles 101 in a way that encourages proper form and muscle mechanics to rotate rope portion 102. This, in turn, increases the stress to a user's upper body, which provides a more challenging and effective workout.

In some embodiments of the present disclosure, each handle 101 may include a bearing 801 and external connector 802 that is external to handle 101. Bearing 801 may be a plain bearing, such as a bushing, a ball bearing, a rolling bearing, an aerostatical or hydrostatical bearing, or any other type of suitable bearing or bearing-like device. External connector 802 may insert through, or otherwise connect or make contact with bearing 801, and may be located at top portion 107 of handle 101. External connector 802, either directly or indirectly, connects each handle 101 to rope portion 102. In some embodiments, external connector 802 may allow a 360-degree rotation of rope portion 102 of jump rope 100 about the x-axis of the handles 101. External connector 802 and rope portion 102 may also be separated, allowing a user to access weighted core 103 within rope portion 102, and to adjust the weight of rope portion 102 (and/or jump rope 100) as the user desires.

The combination of bearing 801 and external connector 802 allows rotation of rope portion 102 about handles 101. In some embodiments, bearing 801 in combination with external connector 802 allows rope portion 102 to rotate 360 degrees relative to the x-axis of handle 101.

Figure 8:
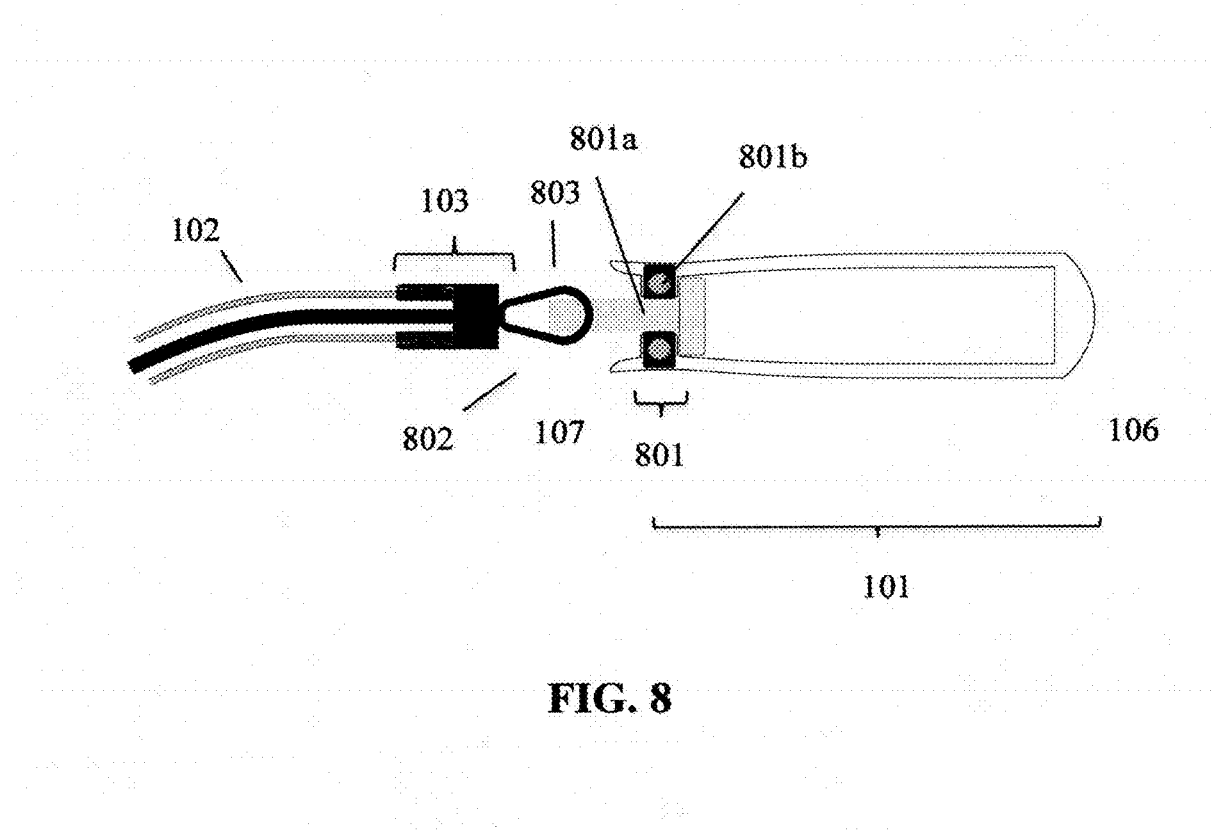
FIG. 8 shows an example of a handle, which includes a bearing and external connector, in accordance with aspects of the present disclosure.

FIG. 8 shows a bearing 801 and external connector 802 in accordance with some embodiments of the present disclosure. Bearing 801 may comprise a circular cavity 801a lined with a plurality of balls 801b. Alternatively, bearing 801 may be a plain bearing, a ball bearing, an aerostatical or hydrostatical bearing, or any other type of bearing or bearing-like device, as would be understood by a person of skill in the art in view of the present disclosure. External connector 802 may comprise a joint pin, and may be inserted through cavity 801a so as to protrude through bearing 801.

External connector 802 may be directly or indirectly connected to rope portion 102. For illustrative purposes, FIG. 8 shows external connector 802 connected to rope portion 102 via weighted core 103, which includes a snap hook 803 that snaps onto external connector 802. A user may separate handle 101 from rope portion 102 by unsnapping hook 803 from external connector 802. Once separated, a user may remove weighted core 103 by unscrewing weighted core 103 from the end of rope portion 102. A user may then insert a different weight weighted core 103, or a cap (not illustrated), which is configured the same as weighted core 103 but does not include extended portion 103a. Alternatively, weighted core 103 may be affixed to rope portion 102 in any number of ways, including as previously described with regard to other embodiments.

In yet another embodiment, external connector 802 may include a loop, ring, shackle and pin, or any other such connector or fastener, that connects, either directly or indirectly, to the end of rope portion 102. Such connector or fastener may be soldered or fused to the end of the rope portion 102 or to a removable end-cap connected to rope portion 102. In some embodiments, such an end-cap may include its own loop, ring, shackle and pin, or any other such fastener. The end-cap and external connector 802 may be looped or chained together to connect external connecter 802 to rope portion 102.

Figure 9:
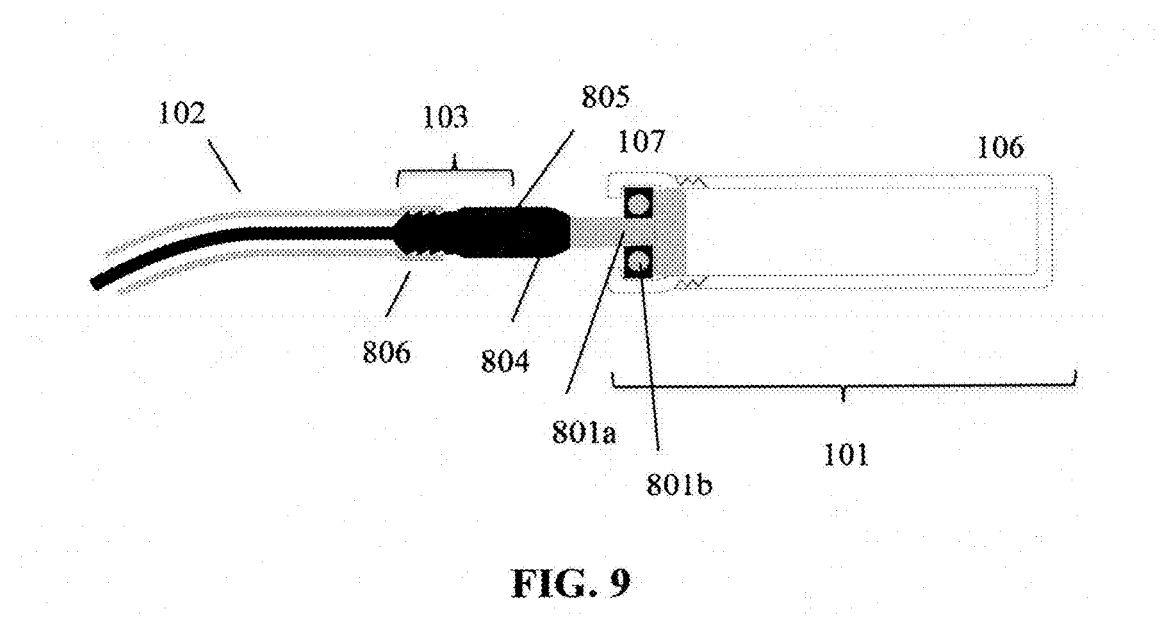
FIG. 9 shows an example of a handle in accordance with aspects of the present disclosure having a connector comprising a joint pin and a female or receiving fitting connected to the weighted core.

In some embodiments, as shown in FIG. 9, external connector 802 comprises a joint pin, as previously described, and a female or receiving fitting 804 connected, directly or indirectly, to weighted core 103. In such an embodiment, weighted core 103 may include a male connector portion 805. Male connector portion 805 may insert into receiving fitting 804, and affix weighted core 103 to handle 101. For illustrative purposes, FIG. 9 shows male connector portion 805 as comprising a screw, or including helical threads or grooves, and as screwing into receiving fitting 804, which includes helical threads for receiving male connector portion 805. But, as would be understood by a person of skill in view of the present disclosure, male connector portion 805 may be affixed to receiving fitting 804 in various ways, including as described with reference to other embodiments.

The end of weighted core 103 opposite the male connector portion 805 may insert into rope portion 102, and may affix rope portion 102 to external connector 802. In some embodiments, weighted core 103 may include a connecting portion 806. Connecting portion 806 connects the rope portion 102 to weighted core 103. For illustrative purposes, FIG. 9 shows connecting portion 806 as including helical threads, similar to a screw, but, as would be understood by a person of skill in view of the present disclosure, connecting portion 806 may be affixed to rope portion 102 in various ways, including as already described herein with reference to the various embodiments of weighted core 103.

Figure 10:
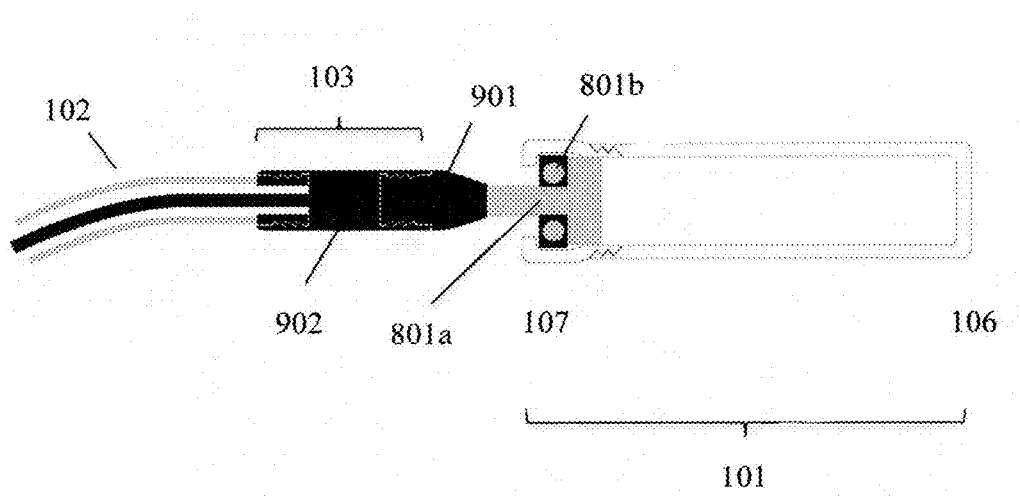
FIG. 10 shows an example of a handle in accordance with aspects of the present disclosure having a connector comprising a joint pin and a male connector portion connected to the weighted core.

FIG. 10, shows an example of an embodiment of the present disclosure utilizing a different rope connector design. External connector 802 may include a male connector portion 901 connected, directly or indirectly, to weighted core 103. In such an embodiment, weighted core 103 may include a female or receiving fitting 902. Male connector portion 901 may insert into receiving fitting 515, and thus affix weighted core 103 to handle 101. For illustrative purposes, FIG. 10 shows male connector portion 901 as comprising a screw, or including helical threads, and as screwing into receiving fitting 902.

With reference to FIG. 1, various portions of rope portion 102 may be fortified with higher-durability materials. For example, aramids, such as Kevlar, Nomex, or Technora, may be added to rope portion 102 in those areas where rope portion 102 may have a tendency to wear, including in areas where rope portion 102 contacts handle 101, the connector(s) (e.g., first connector 109, second connector 501, etc.), and/or the floor. Adding more durable materials helps mitigate wear and tear to those areas of rope portion 102.

In normal use, rope portion 102 has a tendency to strike the ground when passing underneath the user. With continued use, this constant striking may wear rope portion 102 at the areas that make contact with the ground. In some embodiments of this disclosure, a higher-durability material, such as an aramid, including Kevlar, Nomex, or Technora, may be added to the point of contact between rope portion 102 and the ground to help mitigate, if not prevent, such wear.

FIG. 1 shows a sleeve 111 made of a higher-durability material, such as Kevlar, Nomex, Technora or other material as would be apparent to a person of skill in view of the present disclosure, positioned at the point of contact between rope portion 102 and the ground. Sleeve 111 may be held to rope portion 102 using an adhesive or permanent bonding agent. Alternatively, sleeve 111 may be removable. In such an embodiment, sleeve 111 may be held in position through the use of Velcro, or some other mechanical fastener. Alternatively, sleeve 111 may be made of an elastic material. In such an embodiment, sleeve 111 may be held on the rope portion 102 by the compressive force of the elastic material.

In addition to making contact with the ground, rope portion 102 may also have the tendency to make contact with portions of handle 101. This is particular true in the case of new or inexperienced users who may have a tendency to not properly rotate handles 101 when jumping. In some embodiments of this disclosure, to mitigate wear on those areas of rope portion 102 that make contact with handles 101 a higher-durability material, such as an aramid, including Kevlar, Nomex, or Technora, may be added to the point of contact between rope portion 102 and handles 101.

FIG. 1 shows strips 112. Strips 112 may be made of a high-durability material or materials, and may be affixed to the areas of rope portion 102 that have a tendency to make contact with handles 101. In some embodiments of the present disclosure, strips 112 may be affixed to rope portion 102 with an adhesive or bonding agent. In another embodiment, strips 112 may be removable, and may be held in position through the use of Velcro or some other mechanical fastener. Alternatively, strips 112 may be made of an elastic material, and held on the rope portion 102 by the compressive force of such elastic material. In yet another embodiment, the portions of rope portion 102 that make contact with the ground and handle(s) 101 may be made of a thicker material and/or material with a higher durometer value than the remaining areas of rope portion 102.

To further mitigate wear to the portions of rope portion 102 that make contact with handle(s) 101, a material having a low coefficient of friction may be added to handles 101 at the points of contact. Such materials may be permanently affixed to handles 101. Alternatively, such materials may be removable.

Figure 14:
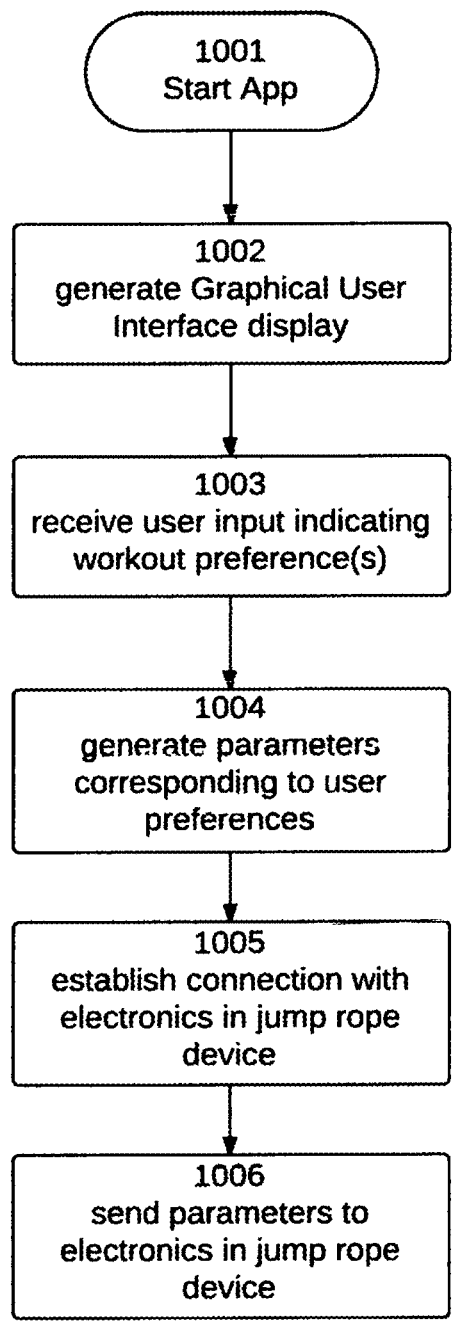
FIG. 14 shows an example of an application running on a consumer electronics device that may interact with electronics disposed in a jump rope device in accordance with aspects of the present disclosure.

FIG. 14 shows an example of an application running on a consumer electronics device that may interact with electronics 300 disposed in a jump rope device. In step 1001, the application may be started, for example, when a user selects the application from a graphical user interface on the consumer electronics device. In step 1002, the application may generate a graphical user interface ("GUI") for display to the user. The GUI may include information downloaded from the Internet, stored in memory of the consumer electronics device, and/or obtained from electronics 300. The GUI may include text, numbers, graphics, illustrations, animations, charts, and/or other display elements to make the display easy to understand and enjoyable to use. In step 1003, the application may receive a user input indicating workout preferences. For example, a user may indicate a desired length of the workout, a desired intensity of the workout, desired goals for the workout, and/or a desired one of a list of preset workouts. In step 1004, the application may generate parameters corresponding to the user preferences. For example, the parameters may correspond to a time, a number of intervals, a duration of intervals, a rotational resistance level, a difficulty level, and/or other metrics. In step 1005, the application may establish a connection with electronics 300 in the jump rope device, for example, via a USB or wireless connection. In step 1006, the parameters may be sent to electronics 300 in the jump rope device; these parameters may then be used by electronics 300 to control a workout and/or to provide feedback to a user. Of course, the application may interact with other software, hardware, and circuitry in the consumer electronics device in performing steps 1001-1006, as one of skill in the art would understand in view of the present disclosure.

It should be understood that, while embodiments of the present disclosure have been described above, the present invention should not be limited by the foregoing. To the contrary, the foregoing written description, figures, and abstract have been presented for illustrative purposes, and are in no way meant to limit the present invention. Indeed, as a person of skill in the art in view of the present disclosure would recognize, various changes can be made to the foregoing without departing from the scope and spirit of the present invention.

What is claimed is:

1. A jump rope device, comprising:
a rope portion comprising a hollow tube;
a first handle disposed on a first end of the rope portion;
a second handle disposed on a second end of the rope portion; and
a flexible weighted core that extends from the first handle through the hollow tube of the rope portion to the second handle,
wherein at least one of the first handle and the second handle comprises a plurality of chambers, wherein each chamber is separated from an adjacent chamber by one of a plurality of dividers, and a specific chamber of said plurality of chambers houses a connector connected to the first end of the rope portion,
wherein the connector comprises an aperture and is capable of rotating within the specific chamber,
wherein a specific divider of the plurality of dividers prevents at least a portion of the connector from entering a specific adjacent chamber which is adjacent to the specific chamber, and
wherein the flexible weighted core comprises an extended portion and a wider portion that together form a T-shape, and the extended portion is disposed within the hollow tube of the rope portion and the aperture of the connector, and the wider portion is disposed outside the rope portion and the aperture.

2. The jump rope device of claim 1, wherein the specific divider comprises an opening.

3. The jump rope device of claim 1, wherein the opening has a smaller diameter than the wider portion of the connector.

4. The jump rope device of claim 1, wherein the plurality of dividers are spaced approximately 0.25 inches apart.

5. The jump rope device of claim 2, wherein the connector further comprises one of a rivet, rivet screw, or T-shaped fastener.

6. The jump rope device of claim 1, wherein the rope portion further comprises a material having a durometer between Shore 68 and Shore 75.

7. The jump rope device of claim 1, wherein the wider portion has a larger diameter than the aperture.

8. The jump rope device of claim 1, wherein the flexible weighted core evenly distributes weight throughout the rope portion.

9. The jump rope device of claim 1, wherein the first handle comprises two pieces connected by a reversible fastener.

10. The jump rope device of claim 1, wherein the flexible weighted core comprises plastic, rubber, elastomer, braided steal, nylon, leather, or cable.

* * * * *